US009016539B2

(12) United States Patent
Kostrzewski et al.

(10) Patent No.: US 9,016,539 B2
(45) Date of Patent: Apr. 28, 2015

(54) MULTI-USE LOADING UNIT

(75) Inventors: Stanislaw Kostrzewski, Newtown, CT (US); Ernest Aranyi, Easton, CT (US); Paul A. Scirica, Huntington, CT (US); William Powers, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 726 days.

(21) Appl. No.: 13/280,880

(22) Filed: Oct. 25, 2011

(65) Prior Publication Data

US 2013/0098965 A1    Apr. 25, 2013

(51) Int. Cl.
*A61B 17/068* (2006.01)
*A61B 17/072* (2006.01)
*A61B 17/00* (2006.01)
*A61B 17/29* (2006.01)
*A61B 19/00* (2006.01)

(52) U.S. Cl.
CPC . *A61B 17/07207* (2013.01); *A61B 2017/00473* (2013.01); *A61B 2017/00477* (2013.01); *A61B 2017/07214* (2013.01); *A61B 2017/07271* (2013.01); *A61B 2017/2927* (2013.01); *A61B 2019/4805* (2013.01); *A61B 2019/4857* (2013.01)

(58) Field of Classification Search
CPC ............. A61B 17/068; A61B 2017/07271
USPC ................................ 227/175.1, 176.1, 19
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |

(Continued)

FOREIGN PATENT DOCUMENTS

| | | |
|---|---|---|
| AU | 5476586 | 9/1986 |
| DE | 2744824 | 4/1978 |

(Continued)

OTHER PUBLICATIONS

European Search Report EP 12 19 2668.7-1654 dated Sep. 20, 2013.

(Continued)

*Primary Examiner* — Michelle Lopez

(57) ABSTRACT

A cartridge assembly is disclosed. The cartridge assembly includes a channel and a removable assembly in releasable engagement with the channel. The removable assembly includes a cartridge body and a support plate. The cartridge body includes an engagement structure disposed adjacent a proximal end thereof. The support plate is configured to mechanically engage the cartridge body and includes an engagement structure disposed adjacent a proximal end thereof. The engagement structure of the cartridge body is configured for longitudinal alignment with the engagement structure of the support plate. The engagement structures of the cartridge body and the engagement structure of the support plate are configured to mechanically engage the engagement structure of the channel when the removable assembly is engaged with the channel.

18 Claims, 25 Drawing Sheets

(56) References Cited

U.S. PATENT DOCUMENTS

| | | |
|---|---|---|
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |

(56) References Cited

U.S. PATENT DOCUMENTS

| | | |
|---|---|---|
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |

(56) References Cited

U.S. PATENT DOCUMENTS

| | | |
|---|---|---|
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielsen et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |

(56) References Cited

U.S. PATENT DOCUMENTS

| | | |
|---|---|---|
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,721,933 B2 | 5/2010 | Ehrenfels et al. |
| 7,726,538 B2 | 6/2010 | Holsten et al. |
| 7,726,539 B2 | 6/2010 | Holsten et al. |
| 7,740,160 B2 | 6/2010 | Viola |
| 7,744,628 B2 | 6/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,760 B2 | 11/2010 | Zemlok et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scirica |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |

(56) References Cited

U.S. PATENT DOCUMENTS

| | | |
|---|---|---|
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,020,742 B2 | 9/2011 | Marczyk |
| 8,028,882 B2 | 10/2011 | Viola |
| 8,028,883 B2 | 10/2011 | Stopek |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 2004/0007608 A1 | 1/2004 | Ehrenfels et al. |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199180 A1 | 10/2004 | Knodel et al. |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2004/0267311 A1 | 12/2004 | Viola et al. |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet |
| 2005/0119669 A1 | 6/2005 | Demmy |
| 2005/0127131 A1 | 6/2005 | Mastri |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184121 A1 | 8/2005 | Heinrich |
| 2005/0184123 A1 | 8/2005 | Scirica et al. |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2005/0279804 A1 | 12/2005 | Scirica et al. |
| 2006/0000867 A1 | 1/2006 | Shelton, IV et al. |
| 2006/0000868 A1 | 1/2006 | Shelton, IV et al. |
| 2006/0011699 A1 | 1/2006 | Olson et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0043147 A1 | 3/2006 | Mastri et al. |
| 2006/0049229 A1 | 3/2006 | Milliman et al. |
| 2006/0049230 A1 | 3/2006 | Shelton, IV et al. |
| 2006/0060630 A1 | 3/2006 | Shelton, IV et al. |
| 2006/0081678 A1 | 4/2006 | Ehrenfels et al. |
| 2006/0097026 A1 | 5/2006 | Shelton, IV |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0175375 A1 | 8/2006 | Shelton, IV et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton, IV |
| 2007/0045380 A1 | 3/2007 | Mastri et al. |
| 2007/0068989 A1 | 3/2007 | Shelton, IV |
| 2007/0068990 A1 | 3/2007 | Shelton, IV et al. |
| 2007/0073340 A1 | 3/2007 | Shelton, IV et al. |
| 2007/0073341 A1 | 3/2007 | Smith et al. |
| 2007/0075114 A1 | 4/2007 | Shelton, IV et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton, IV et al. |
| 2007/0084896 A1 | 4/2007 | Doll et al. |
| 2007/0084897 A1 | 4/2007 | Shelton, IV et al. |
| 2007/0084898 A1 | 4/2007 | Scirica |
| 2007/0084899 A1 | 4/2007 | Taylor |
| 2007/0102472 A1 | 5/2007 | Shelton, IV |
| 2007/0102473 A1 | 5/2007 | Shelton, IV |
| 2007/0102474 A1 | 5/2007 | Shelton, IV |
| 2007/0102475 A1 | 5/2007 | Ortiz et al. |
| 2007/0102476 A1 | 5/2007 | Shelton, IV |
| 2007/0106317 A1 | 5/2007 | Shelton, IV |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton, IV |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton, IV et al. |
| 2007/0175947 A1 | 8/2007 | Ortiz et al. |
| 2007/0175948 A1 | 8/2007 | Scirica et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175954 A1 | 8/2007 | Viola |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179528 A1 | 8/2007 | Soltz et al. |
| 2007/0187453 A1 | 8/2007 | Smith et al. |
| 2007/0187454 A1 | 8/2007 | Scirica |

(56) References Cited

U.S. PATENT DOCUMENTS

| | | |
|---|---|---|
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0179375 A1 | 7/2008 | Scirica |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0050671 A1 | 2/2009 | Racenet et al. |
| 2009/0057370 A1 | 3/2009 | Marczyk et al. |
| 2009/0065549 A1 | 3/2009 | Viola |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok et al. |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green et al. |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0134199 A1 | 5/2009 | Heinrich et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffen et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1 | 11/2009 | Viola et al. |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0314820 A1 | 12/2009 | Green et al. |
| 2009/0314821 A1 | 12/2009 | Racenet |
| 2010/0001036 A1 | 1/2010 | Marczyk et al. |
| 2010/0006620 A1 | 1/2010 | Sorrentino et al. |
| 2010/0012702 A1 | 1/2010 | Marczyk |
| 2010/0012703 A1 | 1/2010 | Calabrese et al. |
| 2010/0012704 A1 | 1/2010 | Tarinelli Racenet et al. |
| 2010/0025452 A1 | 2/2010 | Whitman |
| 2010/0032470 A1 | 2/2010 | Hess et al. |
| 2010/0044411 A1 | 2/2010 | Viola |
| 2010/0065605 A1 | 3/2010 | Shelton et al. |
| 2010/0065606 A1 | 3/2010 | Stopek et al. |
| 2010/0065608 A1 | 3/2010 | Olson et al. |
| 2010/0069942 A1 | 3/2010 | Shelton, IV et al. |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072255 A1 | 3/2010 | Olson et al. |
| 2010/0072256 A1 | 3/2010 | Baxter, III et al. |
| 2010/0072257 A1 | 3/2010 | Farascioni |
| 2010/0072258 A1 | 3/2010 | Farascioni et al. |
| 2010/0076429 A1 | 3/2010 | Heinrich |
| 2010/0076459 A1 | 3/2010 | Farascioni |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096432 A1 | 4/2010 | Scirica |

(56) References Cited

U.S. PATENT DOCUMENTS

| | | |
|---|---|---|
| 2010/0096433 A1 | 4/2010 | Mastri et al. |
| 2010/0096434 A1 | 4/2010 | Viola et al. |
| 2010/0108739 A1 | 5/2010 | Holsten et al. |
| 2010/0116867 A1 | 5/2010 | Balbierz et al. |
| 2010/0116868 A1 | 5/2010 | Prommersberger |
| 2010/0127040 A1 | 5/2010 | Smith et al. |
| 2010/0127041 A1 | 5/2010 | Morgan et al. |
| 2010/0127042 A1 | 5/2010 | Shelton, IV |
| 2010/0127043 A1 | 5/2010 | Olson et al. |
| 2010/0133317 A1 | 6/2010 | Shelton, IV et al. |
| 2010/0133318 A1 | 6/2010 | Boudreaux |
| 2010/0133319 A1 | 6/2010 | Milliman et al. |
| 2010/0133321 A1 | 6/2010 | Racenet et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0163596 A1 | 7/2010 | Marczyk |
| 2010/0163597 A1 | 7/2010 | Shah et al. |
| 2010/0170931 A1 | 7/2010 | Viola |
| 2010/0170933 A1 | 7/2010 | Ivanko |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0237131 A1 | 9/2010 | Milliman et al. |
| 2010/0237133 A1 | 9/2010 | Shah |
| 2010/0243706 A1 | 9/2010 | Cohen et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0243710 A1 | 9/2010 | Mastri et al. |
| 2010/0243711 A1 | 9/2010 | Olson et al. |
| 2010/0249802 A1 | 9/2010 | May et al. |
| 2010/0252610 A1 | 10/2010 | Viola |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0270356 A1 | 10/2010 | Holsten et al. |
| 2010/0282816 A1 | 11/2010 | Scirica et al. |
| 2010/0282817 A1 | 11/2010 | Ehrenfels et al. |
| 2010/0282819 A1 | 11/2010 | Racenet et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308099 A1 | 12/2010 | Marczyk et al. |
| 2010/0308100 A1 | 12/2010 | Boudreaux |
| 2010/0320252 A1 | 12/2010 | Viola et al. |
| 2010/0320253 A1 | 12/2010 | Marczyk |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0024480 A1 | 2/2011 | Marczyk |
| 2011/0024887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036893 A1 | 2/2011 | Viola |
| 2011/0036895 A1 | 2/2011 | Marczyk et al. |
| 2011/0042439 A1 | 2/2011 | Johnson et al. |
| 2011/0042440 A1 | 2/2011 | Holsten et al. |
| 2011/0042441 A1 | 2/2011 | Shelton, IV et al. |
| 2011/0062212 A1 | 3/2011 | Shelton, IV et al. |
| 2011/0062213 A1 | 3/2011 | Scirica et al. |
| 2011/0068144 A1 | 3/2011 | Krehel |
| 2011/0068145 A1 | 3/2011 | Bedi et al. |
| 2011/0068146 A1 | 3/2011 | Viola et al. |
| 2011/0068148 A1 | 3/2011 | Hall et al. |
| 2011/0079626 A1 | 4/2011 | Viola et al. |
| 2011/0079628 A1 | 4/2011 | Racenet et al. |
| 2011/0084112 A1 | 4/2011 | Kostrzewski |
| 2011/0084113 A1 | 4/2011 | Bedi et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089220 A1 | 4/2011 | Ingmanson et al. |
| 2011/0089221 A1 | 4/2011 | Masiakos et al. |
| 2011/0095067 A1 | 4/2011 | Ohdaira |
| 2011/0101066 A1 | 5/2011 | Farascioni et al. |
| 2011/0101067 A1 | 5/2011 | Johnson et al. |
| 2011/0101069 A1 | 5/2011 | Bombard et al. |
| 2011/0101070 A1 | 5/2011 | Bettuchi et al. |
| 2011/0108603 A1 | 5/2011 | Racenet et al. |
| 2011/0108605 A1 | 5/2011 | Sapienza |
| 2011/0108606 A1 | 5/2011 | Whitman |
| 2011/0114702 A1 | 5/2011 | Farascioni |
| 2011/0121049 A1 | 5/2011 | Malinouskas et al. |
| 2011/0121050 A1 | 5/2011 | Nicholas et al. |
| 2011/0121051 A1 | 5/2011 | Shelton, IV et al. |
| 2011/0121052 A1 | 5/2011 | Shelton, IV et al. |
| 2011/0132960 A1 | 6/2011 | Whitman et al. |
| 2011/0132961 A1 | 6/2011 | Whitman et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155784 A1 | 6/2011 | Shelton, IV et al. |
| 2011/0155785 A1 | 6/2011 | Laurent et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163148 A1 | 7/2011 | Wenchell et al. |
| 2011/0163149 A1 | 7/2011 | Viola |
| 2011/0163150 A1 | 7/2011 | Farascioni |
| 2011/0168756 A1 | 7/2011 | Racenet et al. |
| 2011/0168757 A1 | 7/2011 | Viola et al. |
| 2011/0168758 A1 | 7/2011 | Mastri et al. |
| 2011/0168759 A1 | 7/2011 | Prommersberger |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0180586 A1 | 7/2011 | Shah |
| 2011/0184443 A1 | 7/2011 | Tzakis et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0192884 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0233260 A1 | 9/2011 | Milliman et al. |
| 2011/0240711 A1 | 10/2011 | Scirica |
| 2011/0240712 A1 | 10/2011 | Kostrzewski |
| 2011/0240713 A1 | 10/2011 | Scirica et al. |
| 2011/0240714 A1 | 10/2011 | Whitman et al. |
| 2011/0253765 A1 | 10/2011 | Nicholas et al. |

(56) References Cited

U.S. PATENT DOCUMENTS

| | | | |
|---|---|---|---|
| 2011/0253766 | A1 | 10/2011 | Baxter, III et al. |
| 2011/0257679 | A1 | 10/2011 | Ishitsuki et al. |
| 2012/0138660 | A1 | 6/2012 | Shelton, IV |

FOREIGN PATENT DOCUMENTS

| | | |
|---|---|---|
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0 754 433 | 1/1997 |
| EP | 0760230 | 3/1997 |
| EP | 1952769 A2 | 8/2008 |
| EP | 2 165 654 | 3/2010 |
| EP | 2 253 280 | 11/2010 |
| EP | 2 586 382 | 5/2013 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| SU | 659146 | 4/1979 |
| SU | 728848 | 5/1980 |
| SU | 980703 | 12/1982 |
| SU | 990220 | 1/1983 |
| WO | WO8302247 | 7/1983 |
| WO | WO 89/10094 | 11/1989 |
| WO | WO9210976 | 7/1992 |
| WO | 9308754 | 5/1993 |
| WO | 9314706 | 8/1993 |
| WO | 03030743 A2 | 4/2003 |
| WO | WO2008/039238 | 4/2008 |

OTHER PUBLICATIONS

European Search Report for European Application No. EP 13167265 dated Oct. 17, 2013.

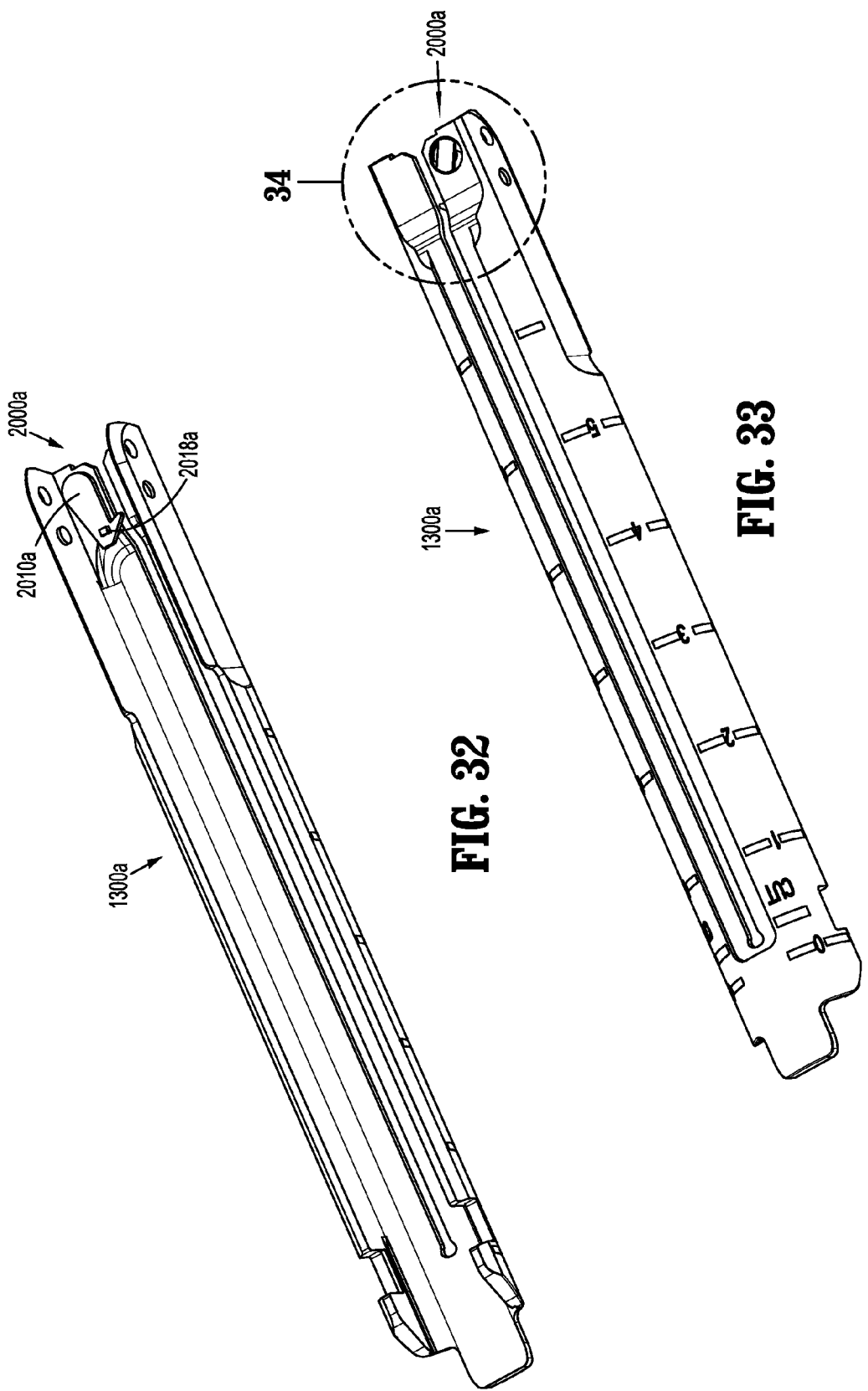

MULTI-USE LOADING UNIT

BACKGROUND

1. Technical Field

The present disclosure relates generally to instruments for surgically joining tissue and, more specifically, to a multi-use loading unit for use with surgical instruments.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

SUMMARY

The present disclosure relates to a surgical instrument having a channel and a removable assembly disposed in releasable engagement with the channel. The removable assembly includes a cartridge body and a support plate. The cartridge body is configured to house a plurality of fasteners or staples therein and includes an engagement structure disposed adjacent a proximal end thereof. The support plate is configured to mechanically engage the cartridge body and includes an engagement structure disposed adjacent a proximal end thereof. The engagement structure of the cartridge body is configured for longitudinal alignment with the engagement structure of the support plate. The engagement structure of the cartridge body and the engagement structure of the support plate are configured to mechanically engage engagement structure of the channel when the removable assembly is engaged with the channel.

In disclosed embodiments, the engagement structure of the channel includes raised bosses, the engagement structure of the cartridge body includes a U-shaped recess, and/or the engagement structure of the support plate includes a U-shaped recess. In disclosed embodiments, the U-shaped recesses of the cartridge body and the support plate include a proximally-facing opening.

In disclosed embodiments, the channel includes a longitudinally-extending slot disposed adjacent a distal end thereof, and the support plate includes an outwardly-extending finger configured to releasably engage the longitudinally-extending slot of the channel.

In disclosed embodiments, the support plate includes an inwardly-extending finger disposed on a distal portion thereof. Here, the inwardly-extending finger is configured to releasably engage a groove disposed on a distal portion of the cartridge body.

In disclosed embodiments, the support plate includes a proximal protrusion disposed adjacent a proximal end thereof. The proximal protrusion is configured to help prevent an actuation sled from prematurely translating distally with respect to the cartridge body.

In certain embodiments, the channel is part of a removable loading unit that includes an anvil assembly.

In a further aspect of the present disclosure, a loading unit for a surgical instrument has an anvil assembly, a channel, and a cartridge assembly. The channel has a boss disposed adjacent a proximal end thereof. The cartridge assembly and anvil assembly are pivotable with respect to one another. The cartridge assembly includes a support plate, and a cartridge body. The support plate is configured to releasably engage the channel and includes a recess disposed adjacent a proximal end thereof. The cartridge body is configured to releasably engage the support plate and is configured to house a plurality of fasteners or staples therein. The cartridge body includes a recess disposed adjacent a proximal end thereof. The recess of the cartridge body is configured for longitudinal alignment with the recess of the support plate. At least one of the recesses of the cartridge body and the support plate is configured to mechanically engage the boss of the channel when the support plate is engaged with the channel.

In disclosed embodiments, the recess of the cartridge body includes a U-shaped recess and/or the recess of the support plate includes a U-shaped recess. In such embodiments, the U-shaped recesses of the cartridge body and the support plate include a proximally-facing opening.

In disclosed embodiments, the channel includes a longitudinally-extending slot disposed adjacent a distal end thereof, and the support plate includes an outwardly-extending finger configured to releasably engage the longitudinally-extending slot of the channel.

In disclosed embodiments, the support plate includes an inwardly-extending finger disposed on a distal portion thereof. The inwardly-extending finger is configured to releasably engage a groove disposed on a distal portion of the cartridge body.

In disclosed embodiments, the support plate includes a proximal protrusion disposed adjacent a proximal end thereof. The proximal protrusion is configured to help prevent an actuation sled from prematurely translating distally with respect to the cartridge body.

In certain embodiments, the loading unit includes a body portion to which the cartridge assembly and anvil assembly are attached the body portion being attachable to the elongate member of a surgical instrument.

The present disclosure also relates to a surgical instrument having a channel and comprising a cartridge assembly, a drive member and a lockout mechanism. The drive member is configured to travel in a distal direction. The lockout mechanism is configured to prevent longitudinal translation of the drive member. The lockout mechanism comprises a latch and a spring. The latch is disposed in mechanical cooperation with the channel and is laterally movable from an initial position to a blocking position. The spring is configured to bias the latch into the blocking position in which a shaped surface of the latch obstructs the distal movement of the drive member when the latch is in the blocking position.

In disclosed embodiments, the latch is pivotable with respect to the cartridge assembly.

In disclosed embodiments, the latch includes a hook configured to engage a portion of the drive member to prevent distal translation of the drive member.

In disclosed embodiments, the latch includes a camming surface, and wherein when the drive member translates proximally into contact with the camming surface, the latch pivots away from its blocking position.

In disclosed embodiments, the surgical instrument comprises a sled configured for longitudinal translation with respect to at least a portion of the cartridge assembly. The sled includes a tail portion that is configured to abut a portion of the latch when the sled is adjacent its proximal-most position. The tail portion of the sled is configured to prevent the latch from moving into its blocking position.

The cartridge assembly may include a cartridge body defining a longitudinal slot. The drive member travels along the longitudinal slot in the distal direction. The shaped surface of the latch is substantially aligned with the longitudinal slot when the latch is in the blocking position.

BRIEF DESCRIPTION OF FIGURES

Various embodiments of the presently disclosed surgical instrument are disclosed herein with reference to the drawings, wherein:

FIGS. 32-35 are perspective views of a second embodiment of a lockout mechanism in accordance with an embodiment of the present disclosure.

DETAILED DESCRIPTION

Figure 1:
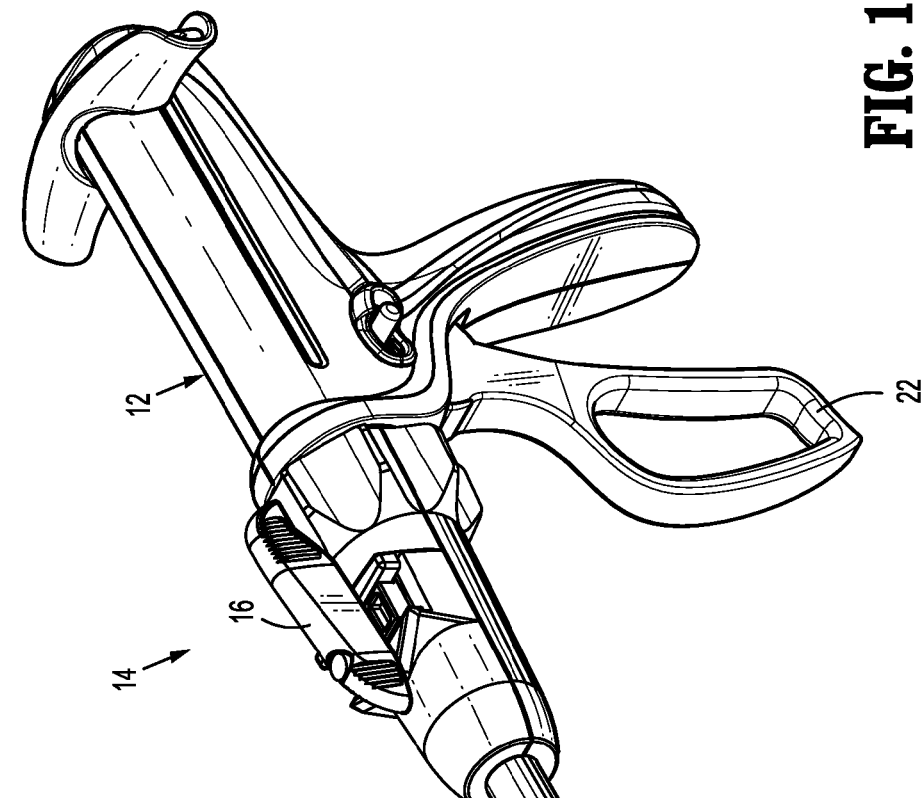
FIG. 1 is a perspective view of a surgical stapling instrument without a loading unit connected thereto in accordance with the present disclosure.
Figure 1A:
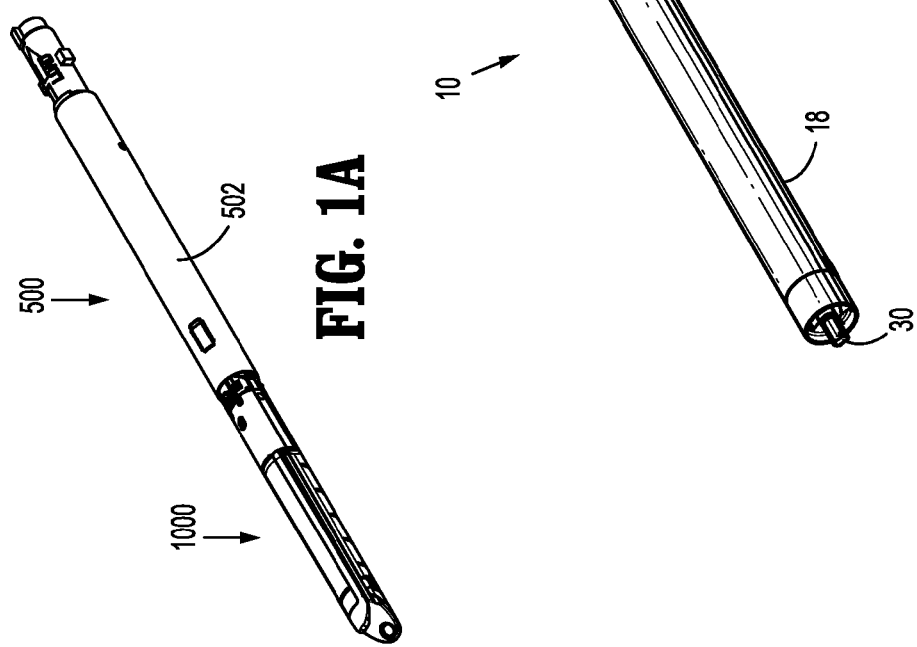
FIG. 1A is a perspective view of a loading unit in accordance with the present disclosure.
Figure 1B:
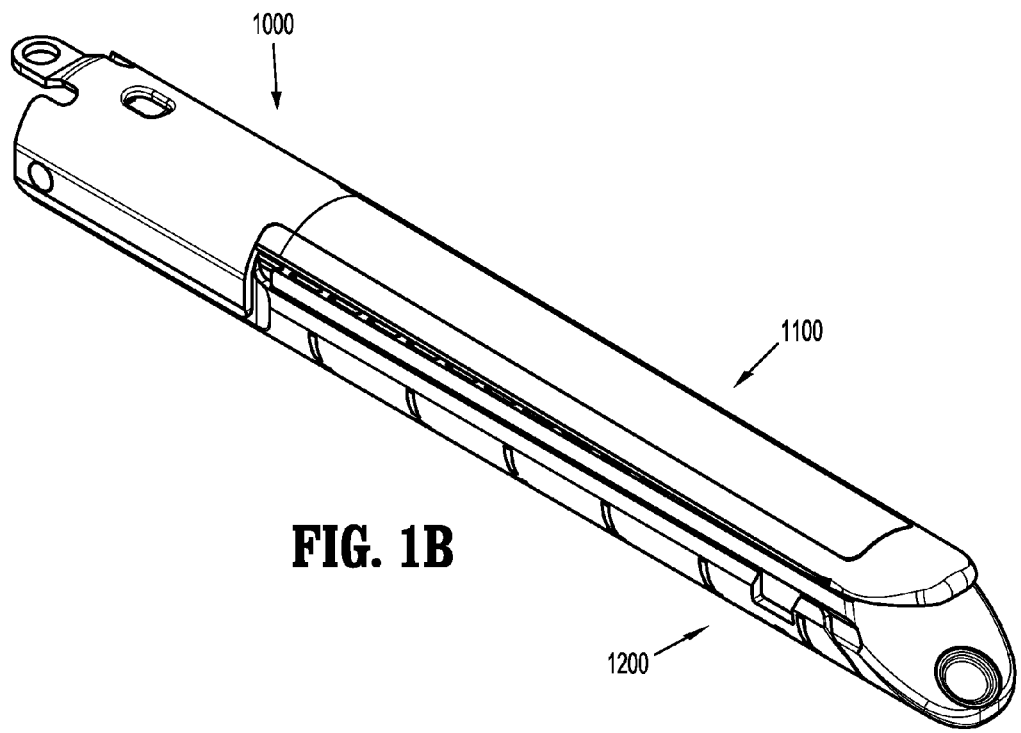
FIG. 1B is a perspective view of a tool assembly of the loading unit of FIG. 1A.
Figure 1C:
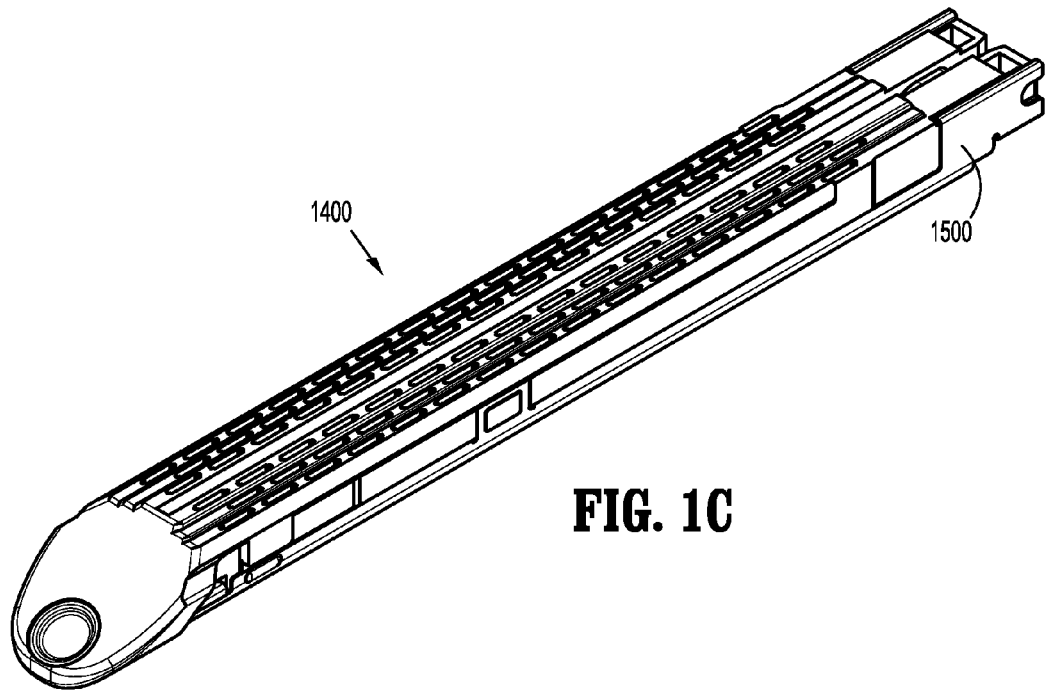
FIG. 1C is a perspective view of a cartridge assembly of the loading unit of FIG. 1A.

Embodiments of the presently disclosed surgical instrument, loading unit and tool assembly for use therewith, are described in detail with reference to the drawings, wherein like reference numerals designate corresponding elements in each of the several views. As is common in the art, the term 'proximal" refers to that part or component closer to the user or operator, e.g., surgeon or physician, while the term "distal" refers to that part or component farther away from the user.

A surgical stapling instrument of the present disclosure is indicated as reference numeral 10 in FIG. 1. Additionally, the depicted surgical instrument fires staples, but it may be adapted to fire any other suitable fastener such as clips and two-part fasteners. A loading unit for use with surgical instrument 10 is shown in the accompanying figures and is indicated as reference number 500. A tool assembly of the loading unit 500 is shown in the accompanying figures and is indicated as reference number 1000.

Loading unit 500 is attachable to an elongated or endoscopic portion 18 of surgical instrument 10, e.g., to allow surgical instrument 10 to have greater versatility. Loading unit 500 of the present disclosure is configured for to be used more than once. In particular, the loading unit has a removable assembly 1600 that includes the cartridge assembly 1200. The cartridge assembly 1200 forms a part of the tool assembly 1000, and the tool assembly 1000 forms a portion of the loading unit 500. The removable assembly is configured to be removed and replaced (e.g., after firing fasteners therefrom). Examples of loading units for use with a surgical stapling instrument are disclosed in commonly-owned U.S. Pat. No. 5,752,644 to Bolanos et al., the entire contents of which are hereby incorporated by reference herein. The loading unit 500 shown includes a proximal body portion 502 that is attachable to an endoscopic portion or an elongated portion 18 of a surgical instrument 10 having a handle assembly 12. However, the features of the loading units 500 of the present disclosure, including the tool assembly 1000, can be incorporated in a surgical instrument in which does not include a detachable portion of the elongated portion of the instrument.

Loading unit 500 includes a proximal body portion 502 and a tool assembly 1000. Proximal body portion 502 defines a longitudinal axis "A-A," and is releasably attachable to a distal end of elongated portion 18 of surgical instrument 10. Tool assembly 1000 includes a pair of jaw members including an anvil assembly 1100 and a cartridge assembly 1200. One jaw member is pivotal in relation to the other to enable the clamping of tissue between the jaw members. In the illustrated embodiments, cartridge assembly 1200 is pivotal in relation to anvil assembly 1100 and is movable between an open or unclamped position and a closed or approximated position. However, the anvil assembly, or both the cartridge assembly and the anvil assembly, can be movable.

Figure 1D:
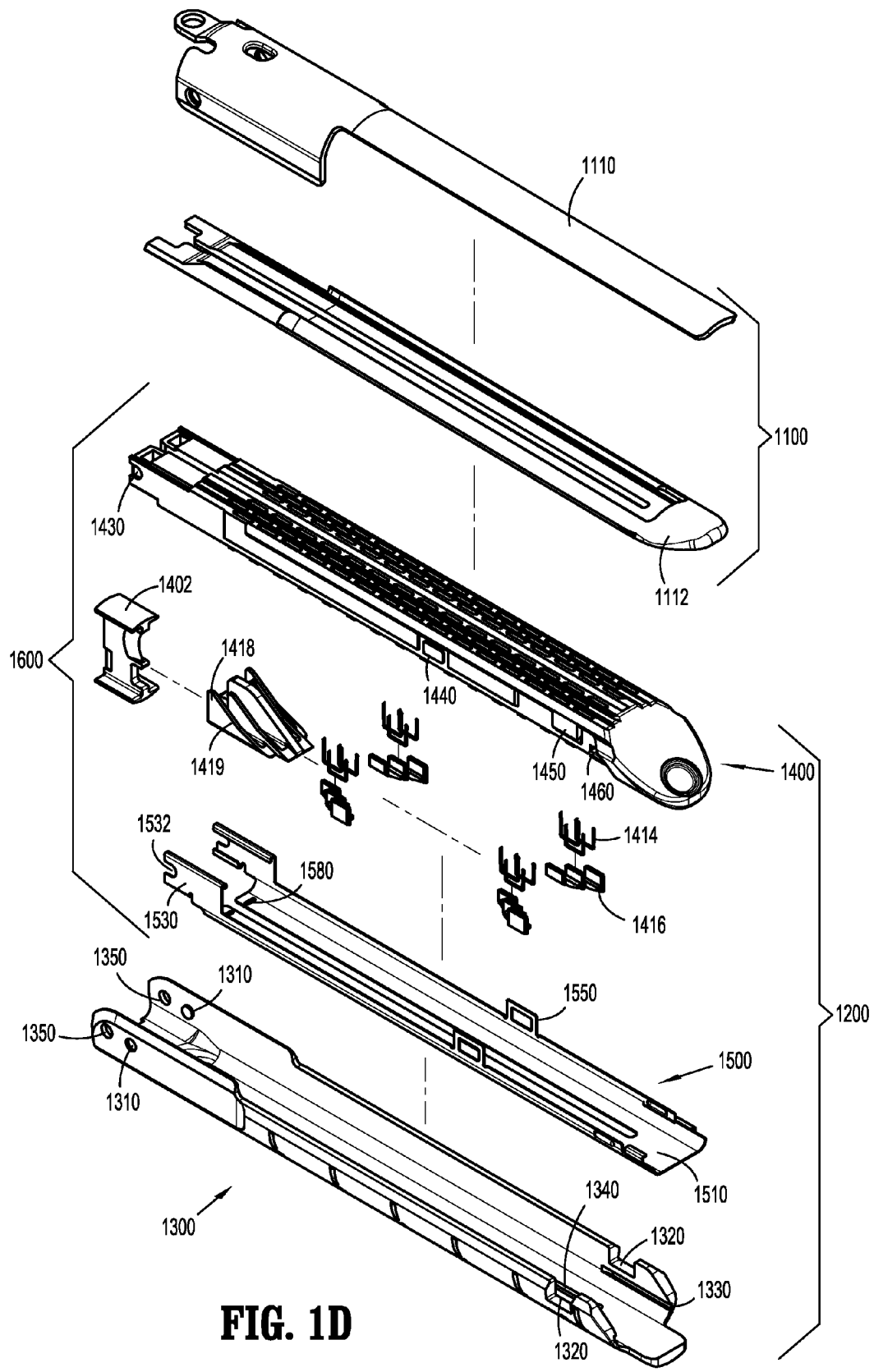
FIG. 1D is an assembly view of the tool assembly of FIG. 1B.
Figure 2:
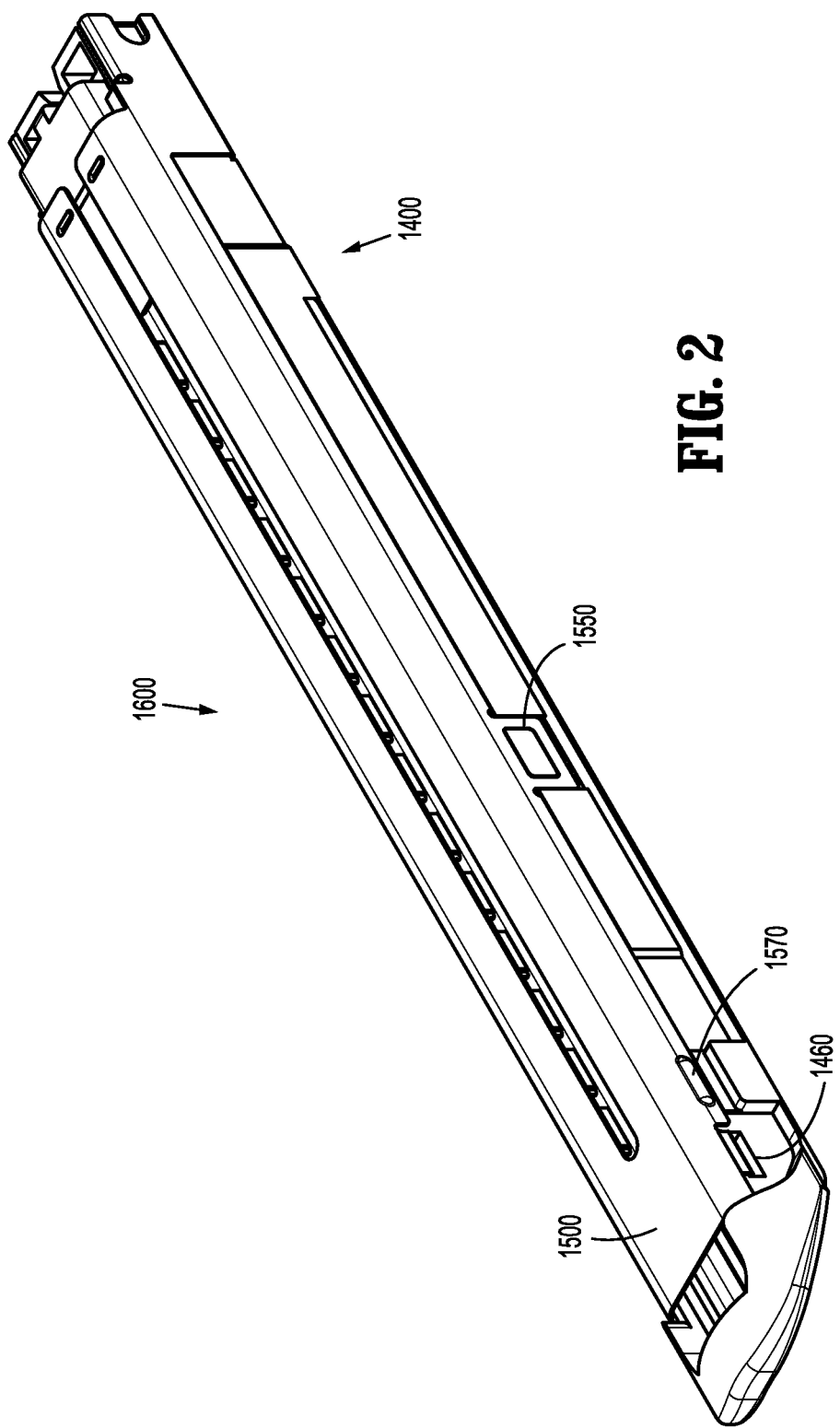
FIG. 2 is a bottom perspective view of a portion of the tool assembly of FIG. 1B.
Figure 8:
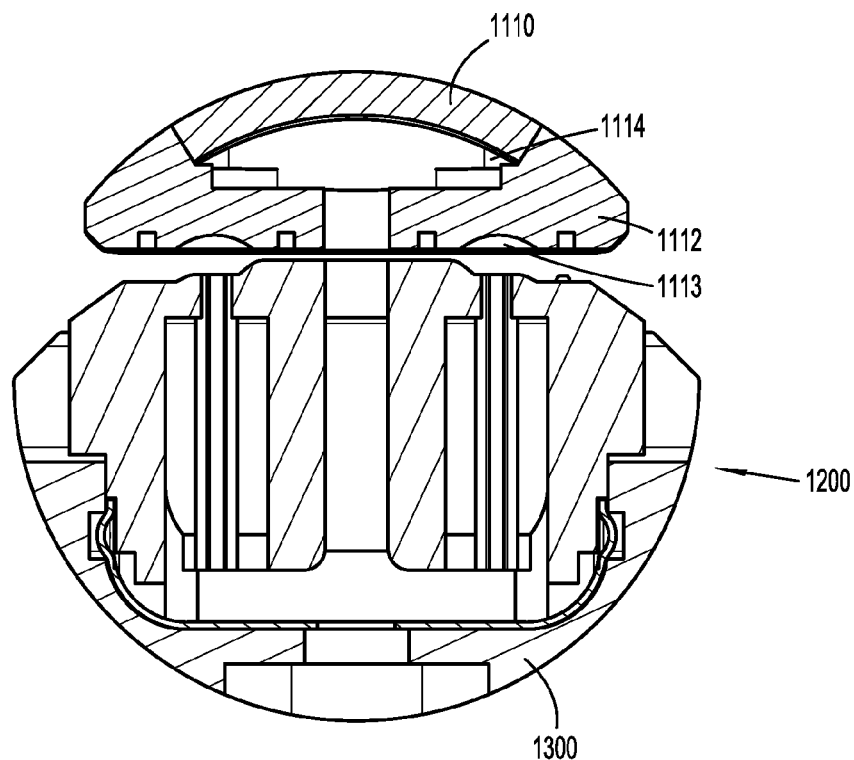
FIG. 8 is a transverse cross-sectional view of portion of the tool assembly of FIG. 1B.

With reference to FIG. 1D, for example, anvil assembly 1100 includes an anvil cover 1110 and an anvil plate 1112, which includes a plurality of staple forming depressions 1113. Anvil plate 1112 is secured to an underside of anvil cover 1110 and defines a channel 1114 (see FIG. 8, for example) therebetween. When tool assembly 1000 is in the approximated position, staple forming depressions 1113 are positioned in juxtaposed alignment with staple receiving slots of the cartridge assembly 1200.

The tool assembly includes a channel or carrier 1300 which receives and supports a cartridge assembly and a support plate 1500. The cartridge assembly has a cartridge body 1400. The cartridge body and support plate 1500 are attached to the channel or carrier 1300 by a snap-fit connection, as discussed below, a detent, latch, or by another type of connection. The cartridge assembly includes fasteners or staples 1414. Cartridge body 1400 defines a plurality of laterally spaced staple retention slots 1410, which are configured as openings in tissue contacting surface 1412 (see FIG. 11). Each slot 1410 is configured to receive a fastener or staple 1414 therein. Cartridge assembly 1200 also defines a plurality of cam wedge slots which accommodate staple pushers 1416 and which are open on the bottom (i.e., away from tissue-contacting surface 1412) to allow an actuation sled 1418 to pass longitudinally therethrough.

Further details of the various components of cartridge assembly 1200, including the connection between its various components, and the removability and replaceability of cartridge body 1400 and support plate 1500 with respect to channel 1300, are discussed below. Generally, the removable assembly 1600 includes cartridge assembly 1200 and support plate 1500. The removable assembly 1600 is removable from channel 1300, e.g., after staples 1414 has been fired from cartridge body 1400. Another removable assembly is capable of being loaded onto channel 1300, such that surgical instrument 10 can be actuated again to fire additional fasteners or staples 1414, for instance.

Figure 6:
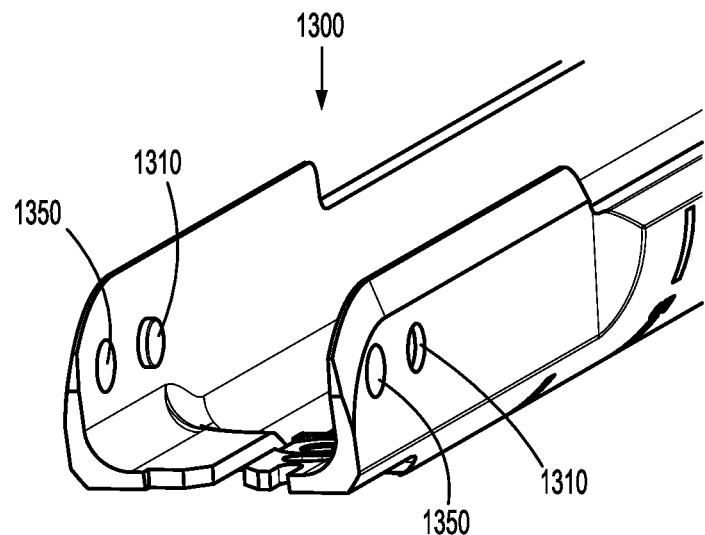
FIG. 6 is a perspective view of a proximal portion of a channel of the tool assembly of FIG. 1B.
Figure 7:
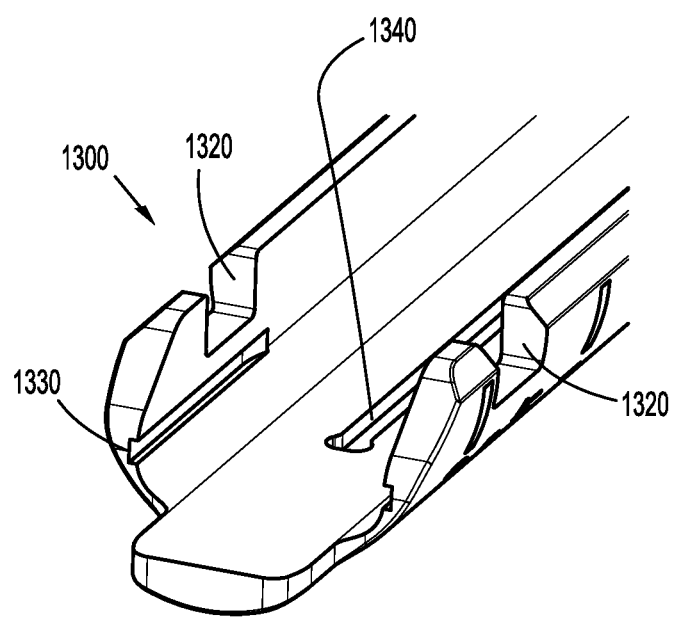
FIG. 7 is a perspective view of a distal portion of the channel of the tool assembly of FIG. 1B.
Figure 9:
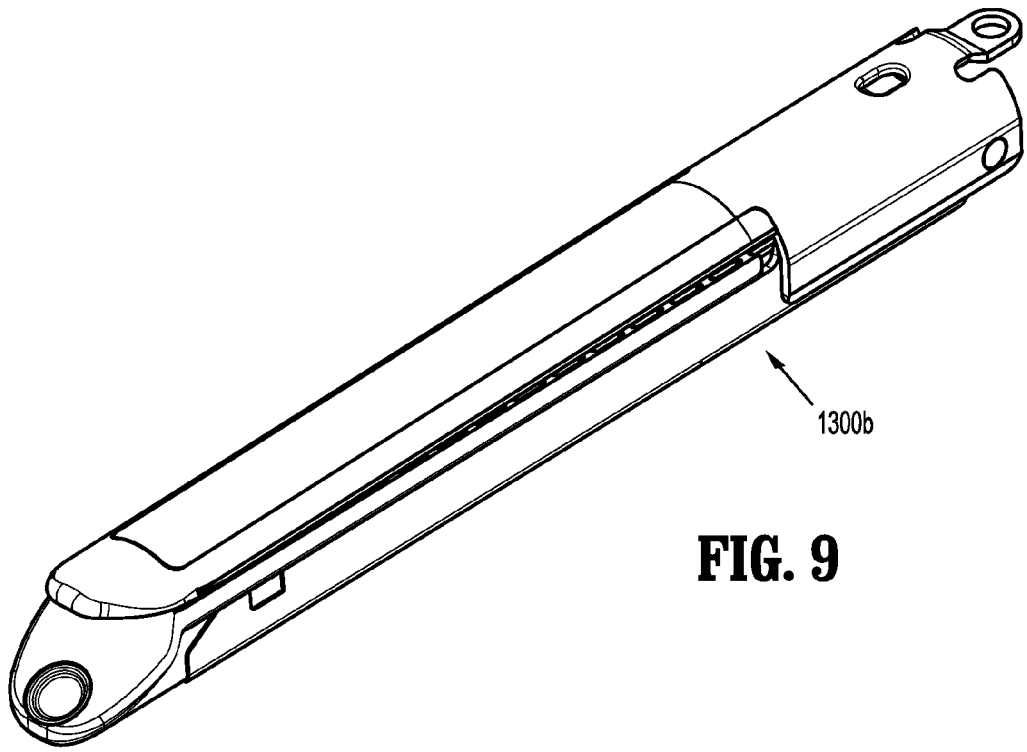
FIG. 9 is a perspective view of the tool assembly of FIG. 1B.

Channel 1300, which may be machined (e.g., e.g., 1300a in FIGS. 13-17) or made of sheet metal (e.g., 1300b in FIG. 9), includes one or a pair of engagement structures or proximal bosses 1310 (e.g., 1300b in FIG. 6), a pair of cut-outs 1320 disposed adjacent a distal end, a pair of distal slots 1330, a central slot 1340, a pair of proximal holes 1350, and a ramped surface 1360. Proximal holes 1350 are configured to align with/mechanically engage a pair of corresponding holes 1120 (e.g., with a pin or protrusion extending through holes 1350 and holes 1120) on anvil cover 1110 to facilitate a pivotal relationship between anvil assembly 1100 and cartridge assembly 1200. It is envisioned that engagement structures 1310 may be pins, protrusions, or similar structure.

Figure 11:
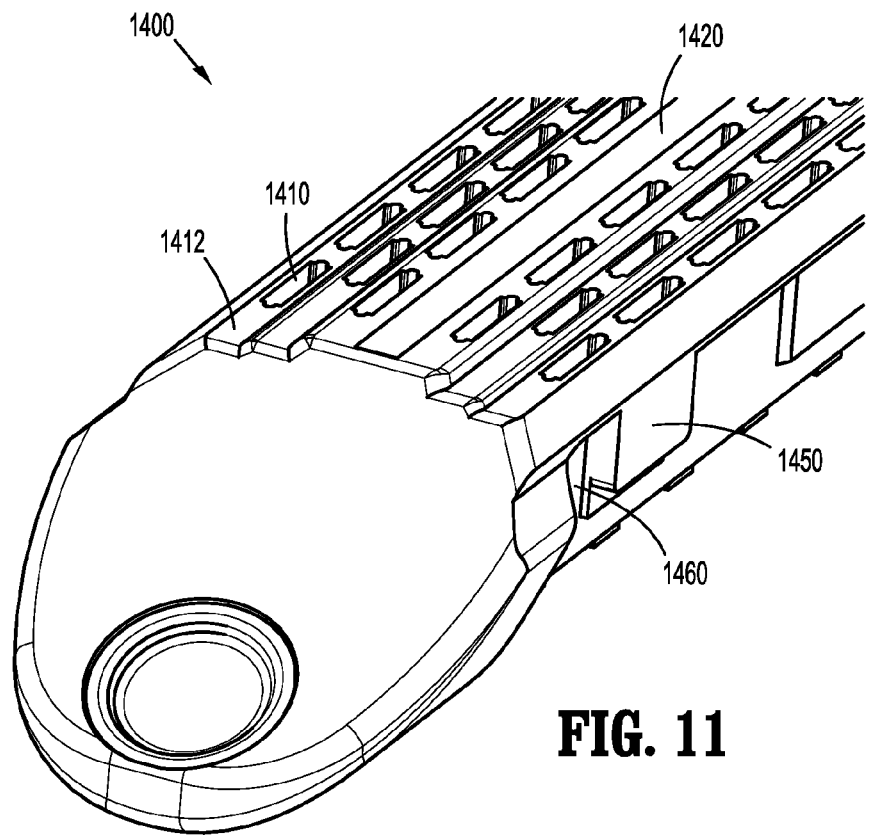
FIG. 11 is a perspective view of a distal portion of a cartridge body of the tool assembly of FIG. 1B.

Cartridge body 1400 includes a central slot 1420, and rows of staple retention slots 1410 positioned on each side of slot 1420 (see FIG. 11). In the illustrated embodiment, three rows of retention slots 1410 are shown. More specifically, cartridge body 1400 is configured such that actuation sled 1418 can pass through the cam wedge slots and force staple pushers 1416 towards anvil plate 1112. The staples 1414, which are supported on the pushers, are then forced out of their respective staple retention slots 1410. Cartridge body 1400 also includes a pair of engagement structures or U-shaped recesses 1430 (which may, in other embodiments, be slots or openings) adjacent its proximal end, a pair of central bosses 1440, a pair of distal protrusions 1450, and a pair of distal grooves 1460. Pairs of upper and lower mounting surfaces 1470, 1480, respectively, are disposed adjacent a proximal end of cartridge body 1400, and are disposed adjacent respective upper and lower mounting slots 1472, 1482.

Figure 10:
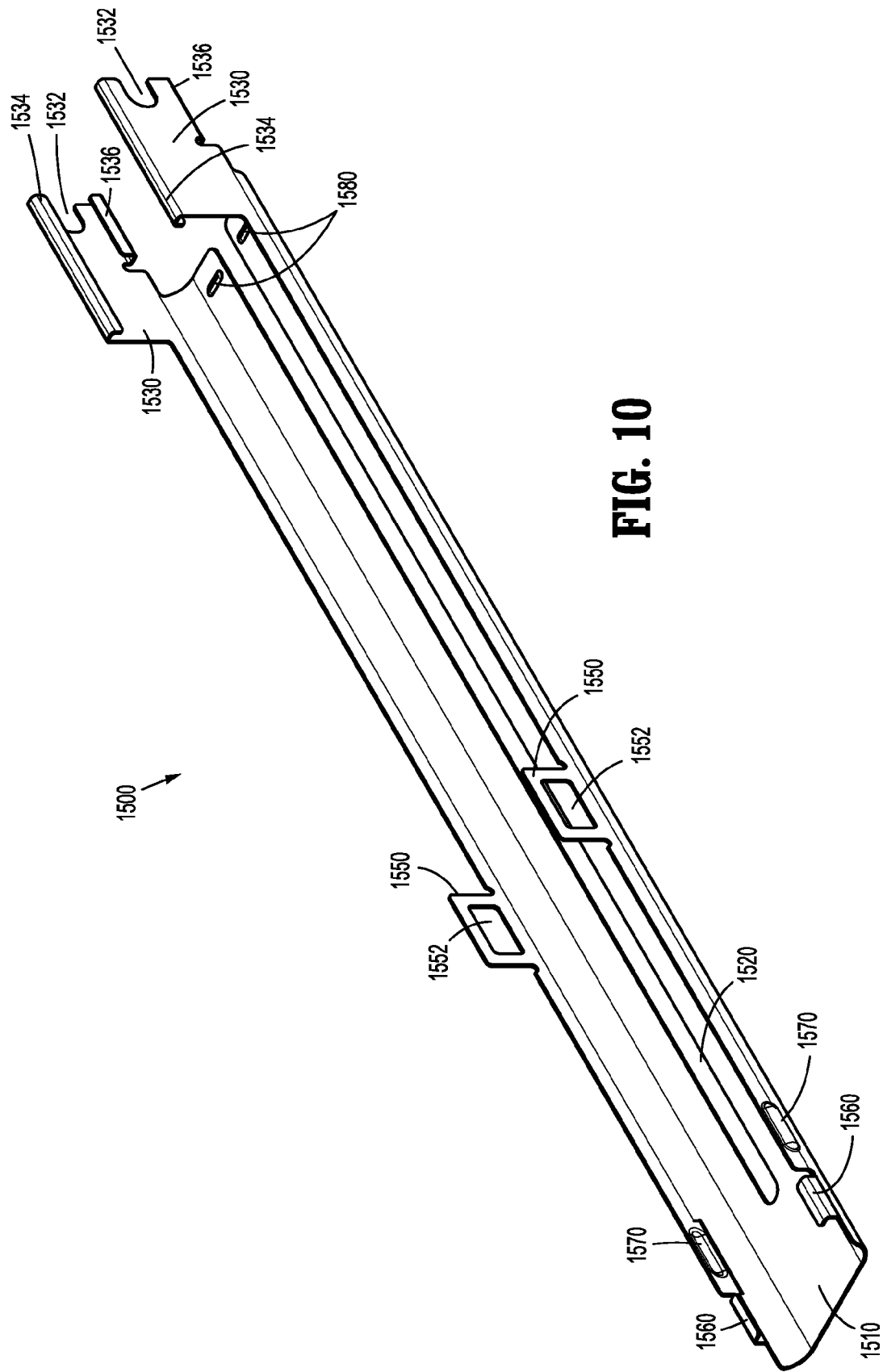
FIG. 10 is a perspective view of a support plate of the tool assembly of FIG. 1B.

With particular reference to FIG. 10, support plate 1500 includes a base surface 1510, a longitudinal slot 1520 extending through base surface 1510, a pair of proximal fingers 1530 disposed and extending substantially perpendicularly from a proximal end of base surface 1510, a pair of intermediate fingers 1550 extending substantially perpendicularly from a middle portion of base surface 1510, a pair of inwardly-extending fingers 1560 and outwardly-extending bosses 1570 disposed adjacent a distal end of base surface 1510, and a pair of proximal protrusions 1580 disposed adjacent the proximal end of base surface 1510. Each proximal finger 1530 includes an engagement structure or proximal-facing U-shaped recesses 1532, an upper mounting flange 1534, and a lower mounting flange 1536. As can be appreciated, support plate 1500 helps maintain pushers 1416 in place with respect to cartridge body 1400. Additionally, longitudinal slot 1520 allows a portion of a drive member to pass through the support plate 1500. The drive member may be a dynamic clamping member 1402. The dynamic clamping member or drive member 1402 drives the actuation sled 1418 through the cartridge body 140. The central slot of the cartridge body, the central slot of the channel, and the longitudinal slot of the support plate are all configured to align with one another to allow the passage of the drive member.

Figure 3:
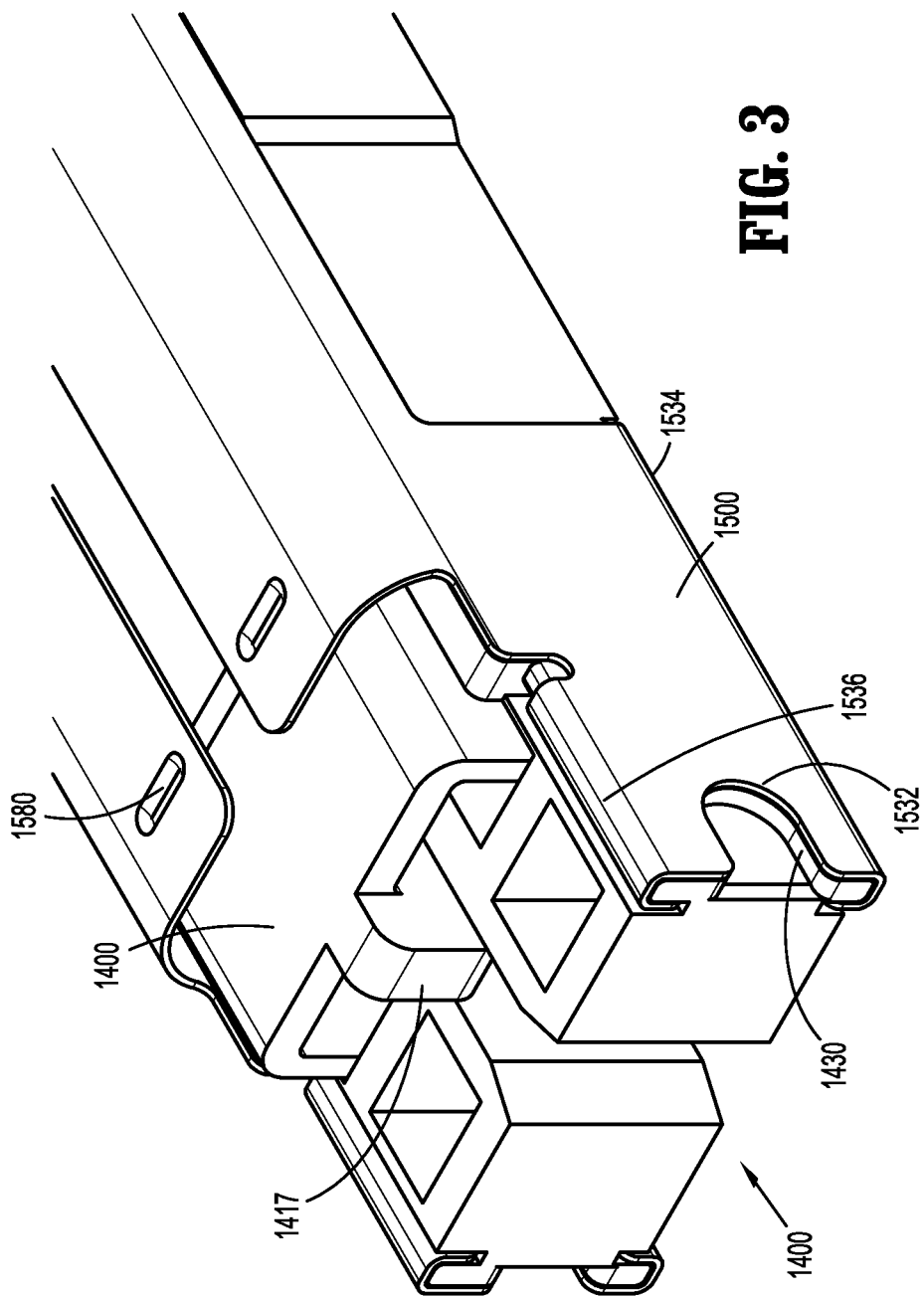
FIG. 3 is a perspective view of a portion of the tool assembly of FIG. 1B.
Figure 4:
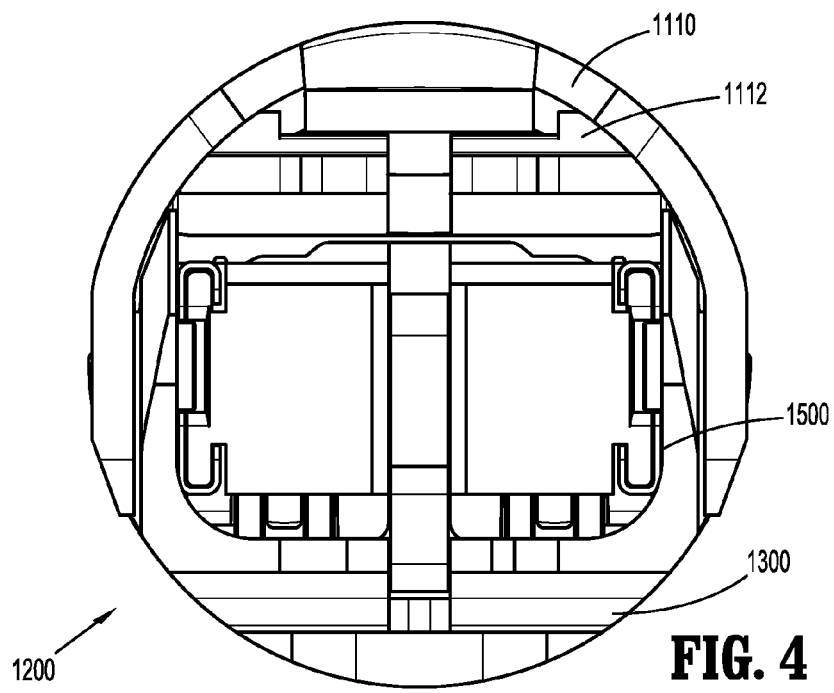
FIGS. 4 and 5 are transverse cross-sectional views of portions of the tool assembly of FIG. 1B.
Figure 5:
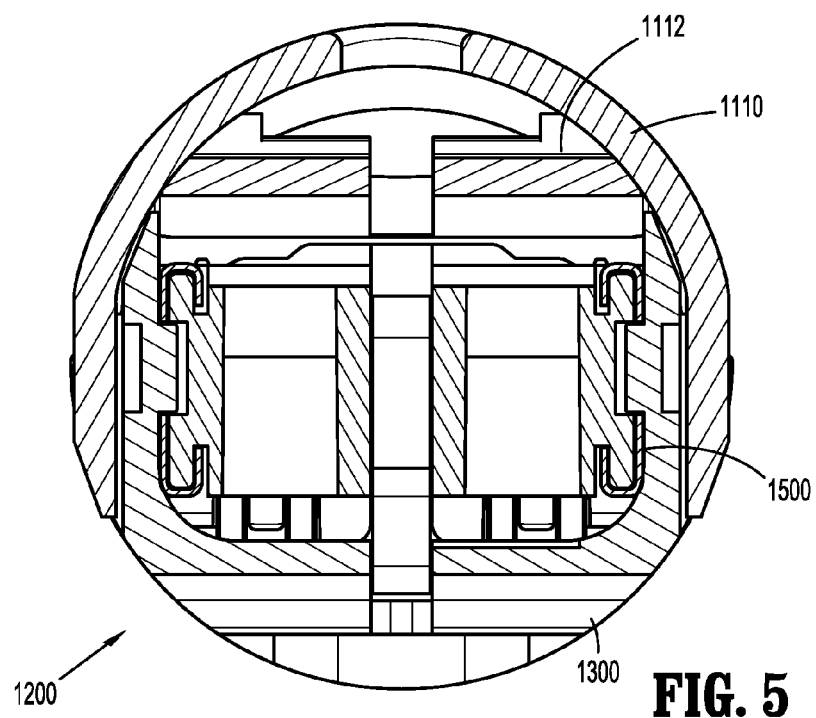
Figure 12:
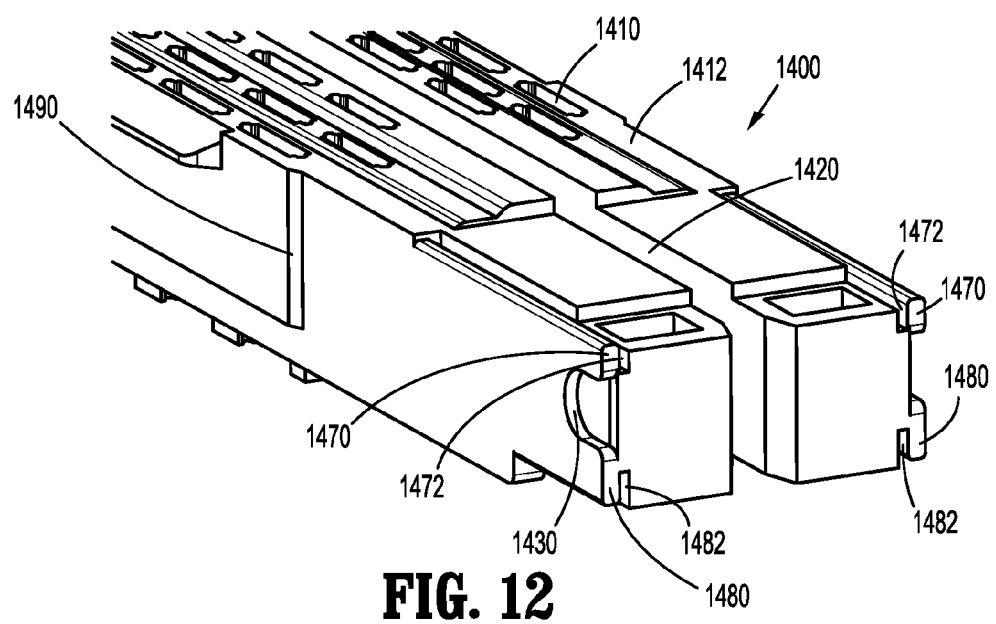
FIG. 12 is a perspective view of a proximal portion of the cartridge body of the tool assembly of FIG. 1B.
Figure 13:
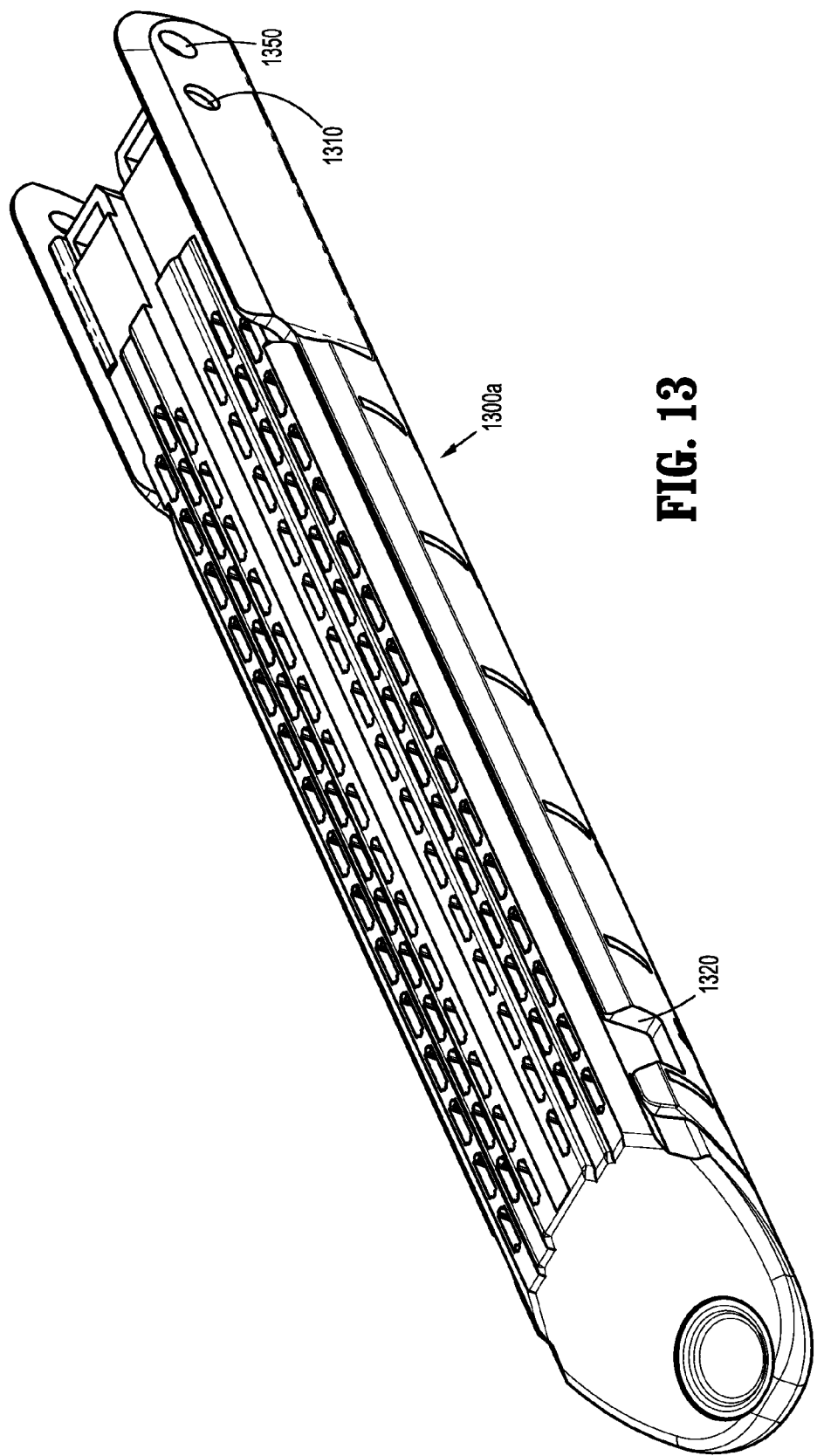
FIG. 13 is a perspective view of a portion of a tool assembly of the present disclosure including another embodiment of a channel.
Figure 14:
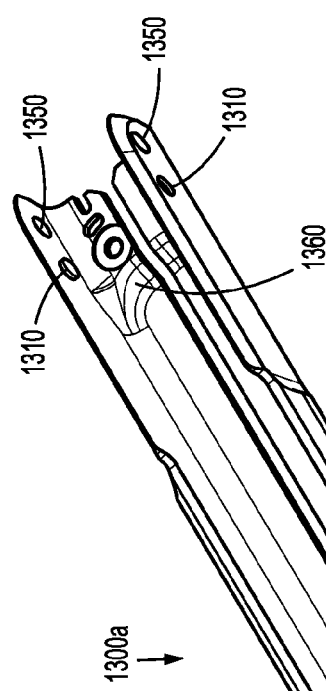
FIGS. 14 and 15 are perspective views of the channel of FIG. 13.
Figure 15:
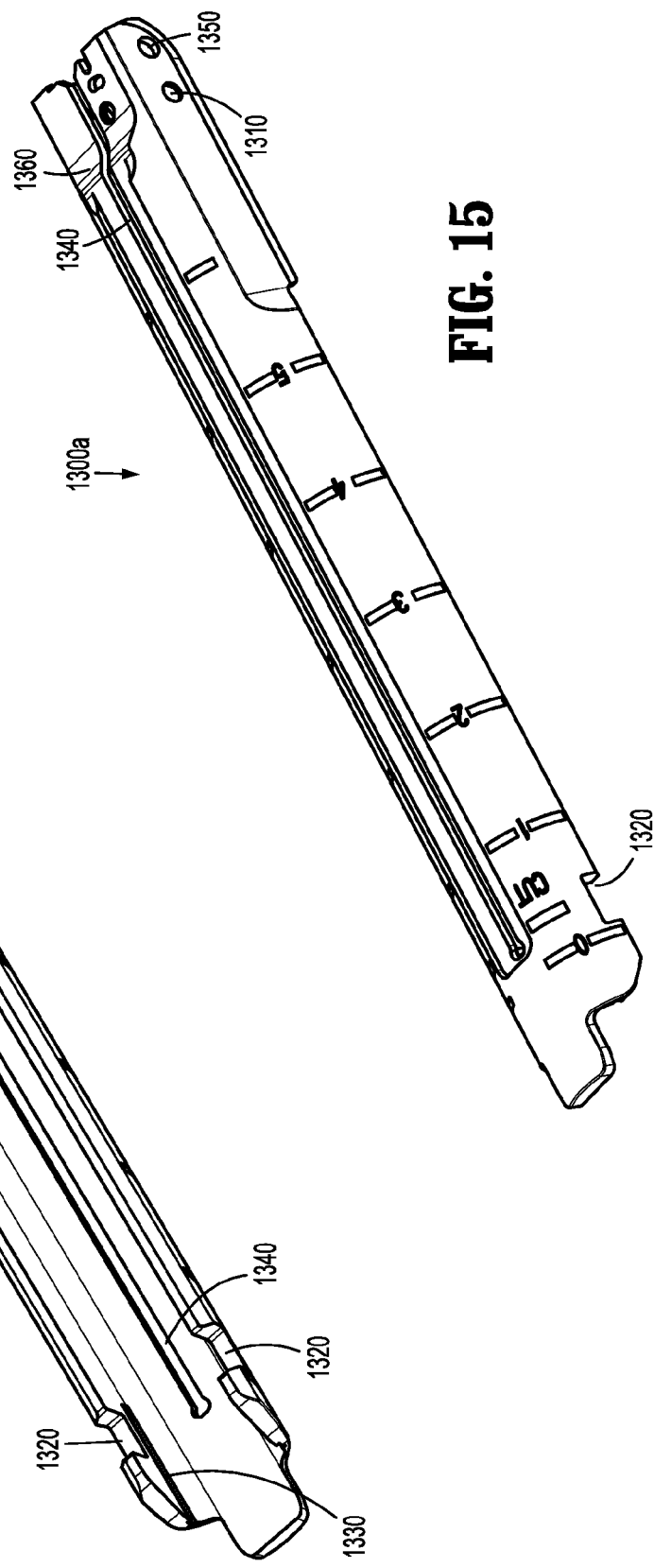
Figure 16:
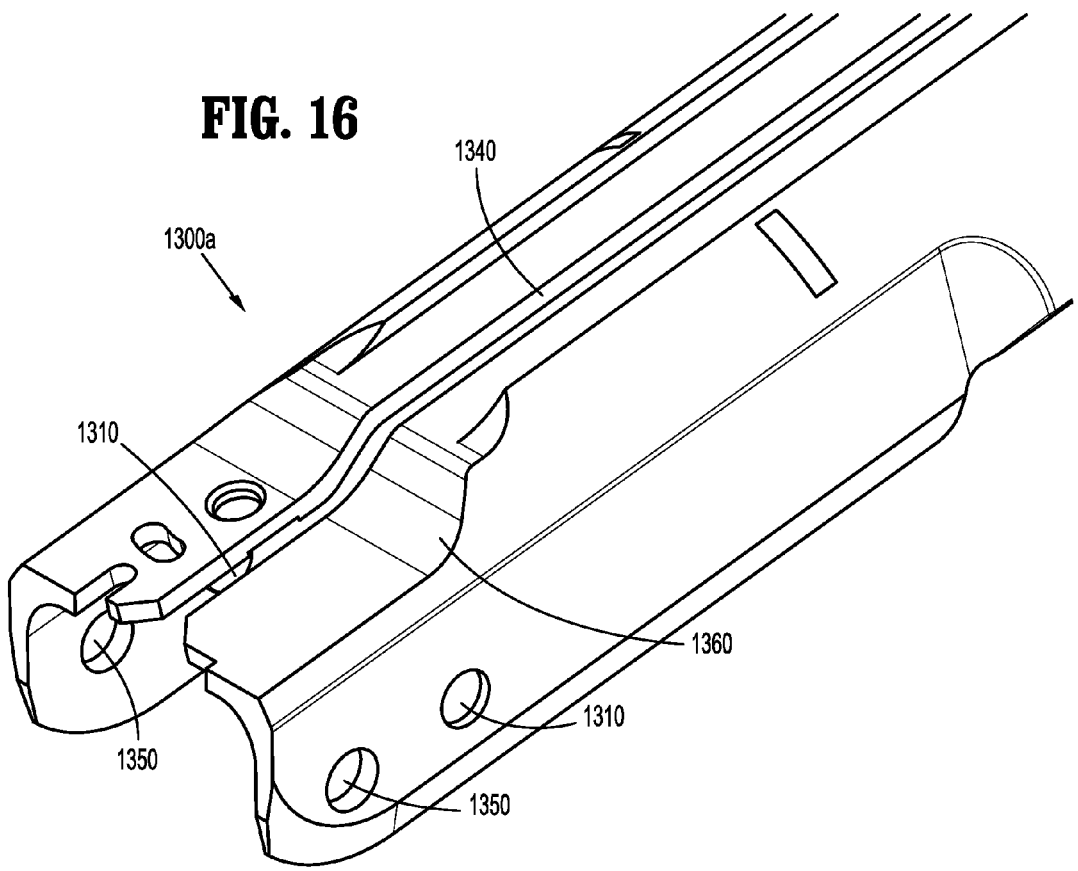
FIGS. 16 and 17 are perspective views of different portions of the channel of FIG. 13.
Figure 17:
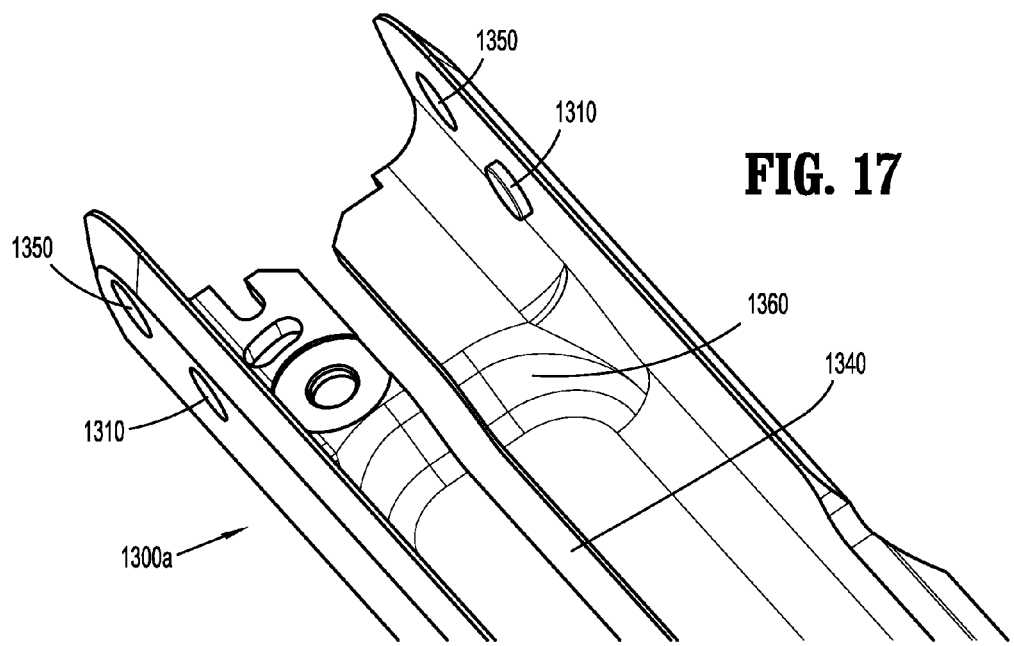
Figure 18:
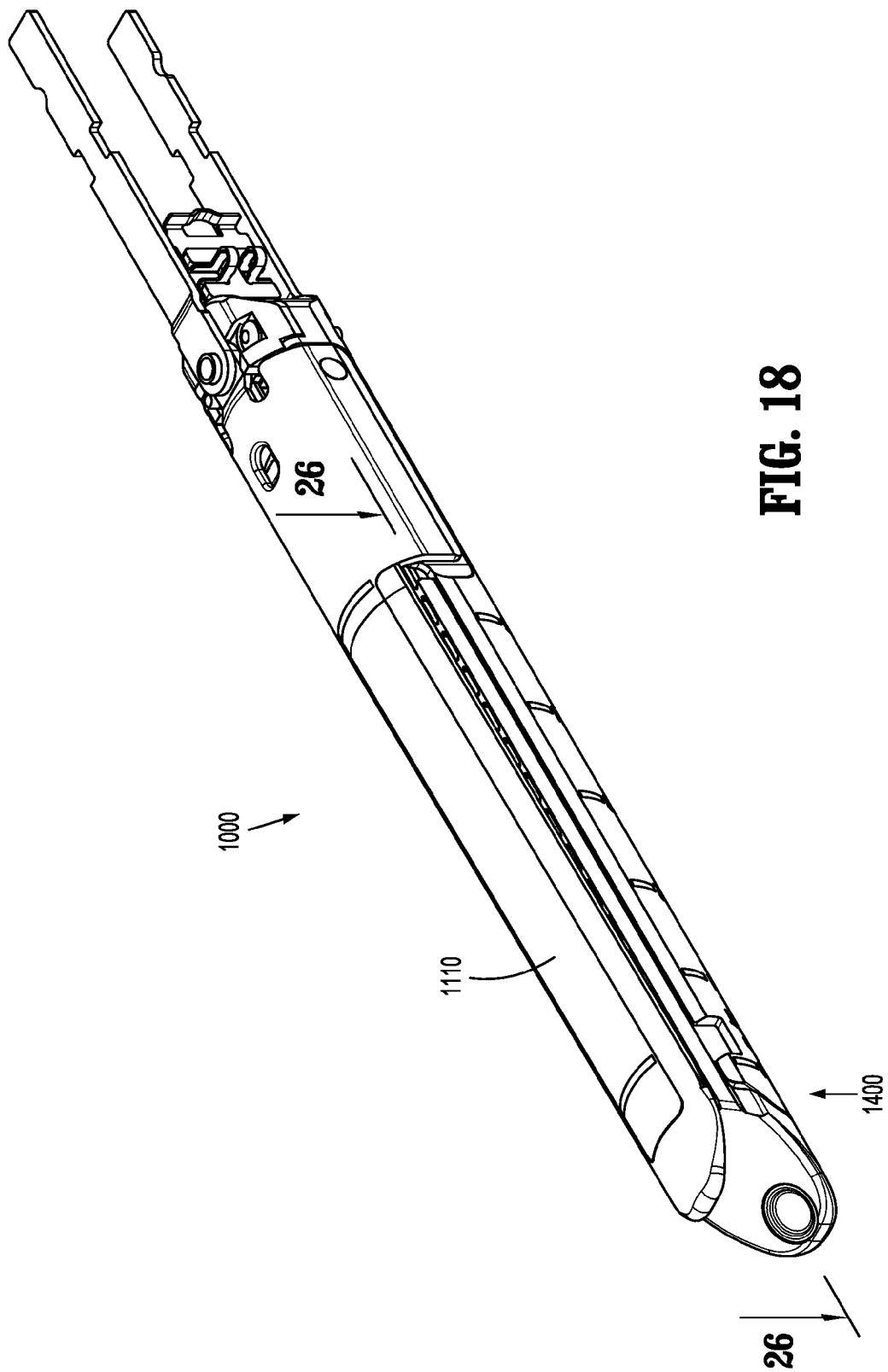
FIG. 18 is a perspective view of a tool assembly of the present disclosure including a lockout mechanism.
Figure 19:
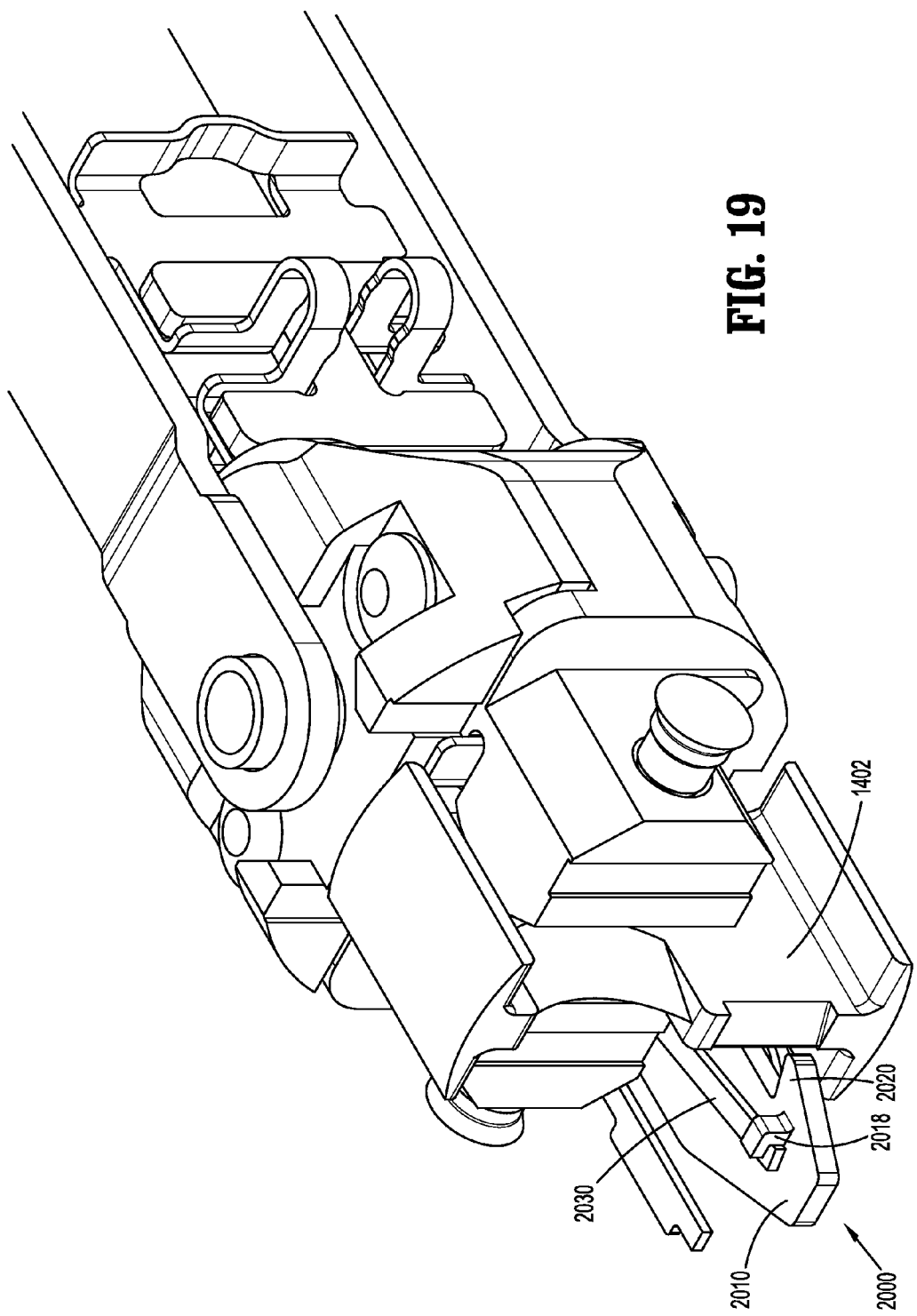
FIG. 19 is an enlarged perspective view of the lockout mechanism of the present disclosure engaged with a portion of the tool assembly.
Figure 20:
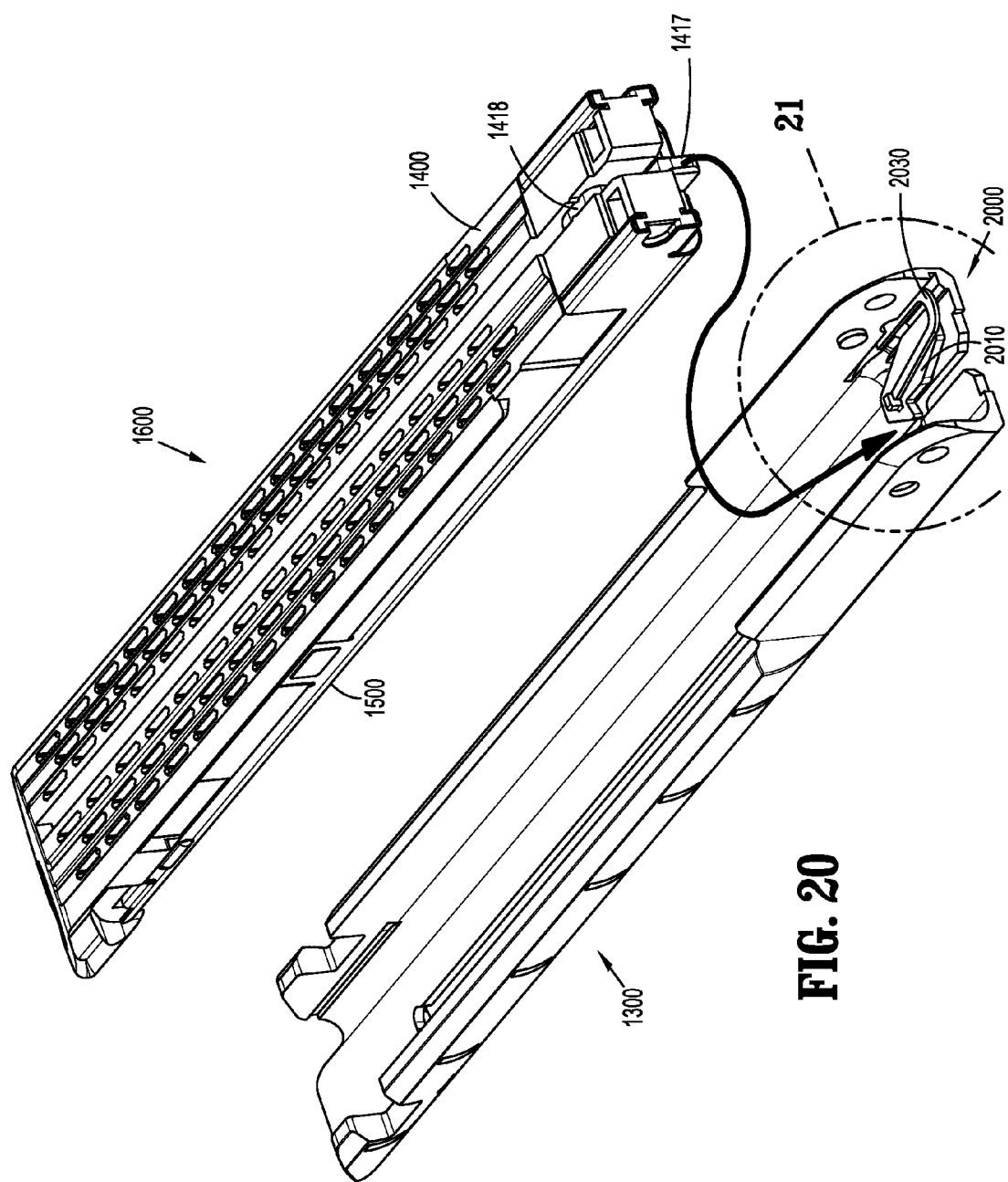
FIG. 20 is a perspective assembly view of portions of the tool assembly includes the lockout assembly.

In use, to connect cartridge body 1400 and support plate 1500, cartridge body 1400 and support plate 1500 are assembled or brought together such that the proximal-most end of cartridge is positioned between proximal fingers 1530 of support plate 1500 and in contact with base surface 1510 thereof. Support plate 1500 is then longitudinally translated (e.g., slid distally) with respect to cartridge body 1400 such that upper mounting flanges 1534 and lower mounting flanges 1536 engage upper mounting slots 1472 and lower mounting slots 1482, respectively. The longitudinal translation between cartridge body 1400 and support plate 1500 continues until a distal-most end of proximal fingers 1530 contact a respective vertical wall 1490 (FIG. 12) of cartridge body 1400. At this stage, U-shaped recesses 1430 are laterally adjacent and aligned with U-shaped recesses 1532 (see FIG. 3), and continued proximal movement of cartridge body 1400 with respect to support plate 1500 is prevented. Next, or concomitantly with the relative longitudinal translation between cartridge body 1400 and support plate 1500, cut-outs 1552 within intermediate fingers 1550 of support plate 1500 are positioned around central bosses 1440 of cartridge, and inwardly-extending fingers 1560 are moved into engagement with distal grooves 1460 of cartridge. Cartridge assembly 1200 and support plate 1500 comprise a removable assembly 1600, which is removable from and replaceable onto channel 1300 by the user of the surgical instrument 10 and/or loading unit 500.

Removable assembly 1600 is insertable onto channel 1300 by approximating removable assembly 1600 and channel 1300 such that proximal bosses 1310 are positioned proximally of U-shaped recesses 1430 and 1532, and such that distal ends of distal slots 1330 are positioned proximally of proximal ends of outwardly-extending bosses 1570. Next, removable assembly 1600 is translated longitudinally (e.g., proximally) with respect to channel 1300 such that outwardly-extending bosses 1570 translate proximally within distal slots 1330 until proximal bosses 1310 contact U-shaped recesses 1430 and 1532. Next, or concomitantly with the relative longitudinal translation between removable assembly 1600 and channel 1300, cut-outs 1320 of channel 1300 are moved into engagement with distal protrusions 1450 of cartridge body 1400. Ramped surface 1360 is engaged by the dynamic clamping member 1402 in order to move the anvil assembly 1100 and the cartridge assembly 1200 with respect to one another. A similar surface could be provided on the anvil assembly 1100, in other embodiments. It is envisioned that ramped surface 1360 may also facilitate the alignment and/or engagement between channel 1300 and support plate 1300 and/or cartridge body 1400.

Once assembled, a user is able to actuate movable handle 22 to eject staples 1414 from cartridge body 1400 and into tissue, as described below. It is envisioned that proximal protrusions 1580, which extend from base surface 1510, help maintain actuation sled 1418 in its relative position with respect to support plate 1500 before actuation of instrument 10. That is, it is envisioned that actuation sled 1418, or a portion thereof, is positioned proximally of proximal protrusions 1580, and that proximal protrusions 1580 form a physically barrier to hinder any premature distal advancement of actuation sled 1418. Once a user intends to actuate instrument 10 and distally advance actuation sled 1418 beyond proximal protrusions 1580, the force used to advance actuation sled 1418 is sufficient to force a lower surface or portion of actuation sled 1418 over proximal protrusions 1580.

After staples 1414 have been ejected from cartridge body 1400, and a user wishes to use the same instrument 10 to fire additional staples 1414 (or another type of fastener or knife), the user can remove the removable assembly 1600 by sliding removable assembly 1600 distally with respect to channel 1300. Next, a user removes the removable assembly 1600 from the channel 1300. Another removable assembly with unfired staples can be loaded into the channel 1300. In other embodiments, a cartridge body of a cartridge assembly can be removable from a support plate after the removable assembly is removed from the channel 1300. The cartridge body is removed by sliding support plate 1500 proximally with respect to cartridge body 1400. Another cartridge body, if desired, may be coupled to the support plate and inserted into the channel.

In certain embodiments, the removable assembly is part of a loading unit 500 that is removably attached to the elongated portion of a surgical stapling instrument, such as elongated portion 18. This enables the user to choose a staple line length that is shorter or longer. It is also contemplated that the removable assembly can be used with a surgical instrument that does not have a loading unit that is removable and instead has jaws permanently attached to the elongated portion 18.

During operation of stapler 10, actuation of its movable handle 22 will fire the staples. The handle assembly 12 has an elongate actuation shaft that is translated distally when the movable handle 22 is pivotally moved by the user. The actuation shaft of the handle assembly can include teeth that are engaged by the movable handle 22, or the handle assembly 12 can include a series of gears for moving the actuation shaft. Alternatively, the handle assembly can include a motorized driver for moving the actuation shaft, or the handle assembly can be attachable to a separate motorized driver.

In certain embodiments, through successive strokes of the movable handle, a drive rod 30 (a distal portion of which is illustrated in FIGS. 1 and 27-31)) is advanced distally, such that drive rod 30 pushes a portion of the drive assembly (which includes the dynamic clamping member 1402) to translate distally through cartridge body 1400. (Further details of how actuation of movable handle 22 causes distal advancement of drive rod 30 are explained in U.S. Pat. No. 6,953,139 to Milliman et al., which is hereby incorporated by reference herein.) Distal movement of the drive assembly, and in particular, the dynamic clamping member or drive member 1402, causes approximation of one jaw member with respect to the other. That is, an upper portion of the dynamic clamping member 1402 travels through the channel 1114 between the anvil plate 1112 and the anvil cover 1110, and a lower portion of the dynamic clamping member 1402 travels below the carrier 1300 of the cartridge assembly 1200, which causes approximation of the anvil assembly 1100 and the cartridge assembly 1200 to clamp tissue therebetween. For example, the channel 1300 may have a lower surface defining a camming surface and the lower portion of the dynamic clamping member 1402 engages the camming surface to pivot the cartridge assembly 1200 toward the anvil assembly 1100.

Additionally, distal translation of the dynamic clamping member 1402 causes the actuation sled 1418 to move distally through cartridge body 1400, which causes cam wedges 1419 of actuation sled 1418 to sequentially engage pushers 1416 to move pushers 1416 vertically within staple retention slots 1410 and eject staples 1414 into staple forming depressions 1113 of anvil plate 1112. Subsequent to the ejection of staples 1414 from retention slots 1410 (and into tissue), a cutting edge of the dynamic clamping member 1402 severs the stapled tissue as the cutting edge travels distally through central slot 1420 of cartridge body 1400.

It is also envisioned, in further embodiments, that an end effector or tool assembly like the end effector or tool assembly 1000 is arranged for articulating between a first position where tool assembly 1000 is aligned with longitudinal axis "A-A," and a second position where tool assembly 1000 is disposed at an angle with respect to longitudinal axis "A-A." For example, the anvil assembly 110 may be pivotally attached to the proximal body portion 502 of a loading unit 500, or pivotably attached to the elongated portion of the instrument. The loading unit includes one or more cables or linkages disposed in the proximal body portion 502 and attached at the tool assembly 1000. When the cable or linkage is displaced, the tool assembly pivots and articulates with respect to the instrument. Further details of providing articulation are described in detail in commonly-owned U.S. Pat. No. 6,953,139 to Milliman et al., the contents of which has previously been incorporated by reference in their entirety. Further, the tool assembly can be configured not to articulate.

Additionally, it is envisioned that instrument 10 is powered by a power source and/or motor. Further details of such a powered surgical instrument are included in U.S. Patent Publication No. 2008/0255607, the entire contents of which are hereby incorporated by reference herein.

Further, and as illustrated in FIG. 11, for example, the present disclosure includes a cartridge body 1400 having a stepped tissue-contacting surface 1412. In such an embodiment, different sized staples 1414, or all the same sized staples, may be used. Further details of a staple cartridge having multiple staple sizes are included in U.S. Pat. No. 7,407,075 to Holsten et al., the entire contents of which are hereby incorporated by reference herein.

The present disclosure also relates to methods of using the described surgical instrument 10, loading unit 500, and tool assembly 100 to perform a surgical procedure and to methods of assembling the various components thereof, as described above.

With reference to FIGS. 18-35, two embodiments of a lockout mechanism 2000, 2000a of the present disclosure are shown. For each of these embodiments, a surgical instrument having the lockout may have a channel, removable assembly, cartridge body, support plate, and the engagement structures discussed above. Furthermore, the present disclosure is directed to a removable assembly having the lockout, or a loading unit having the lockout.

With reference to FIGS. 18-31, the first embodiment of lockout mechanism 2000 includes a latch 2010 and a spring 2030, and is configured to prevent re-firing of cartridge body 1400 of removable assembly 1600, and also prevent distal translation of dynamic clamping member 1402 after an initial distal translation of knife and prior to another removable assembly 1600 being loaded onto channel 1300.

Figure 22:
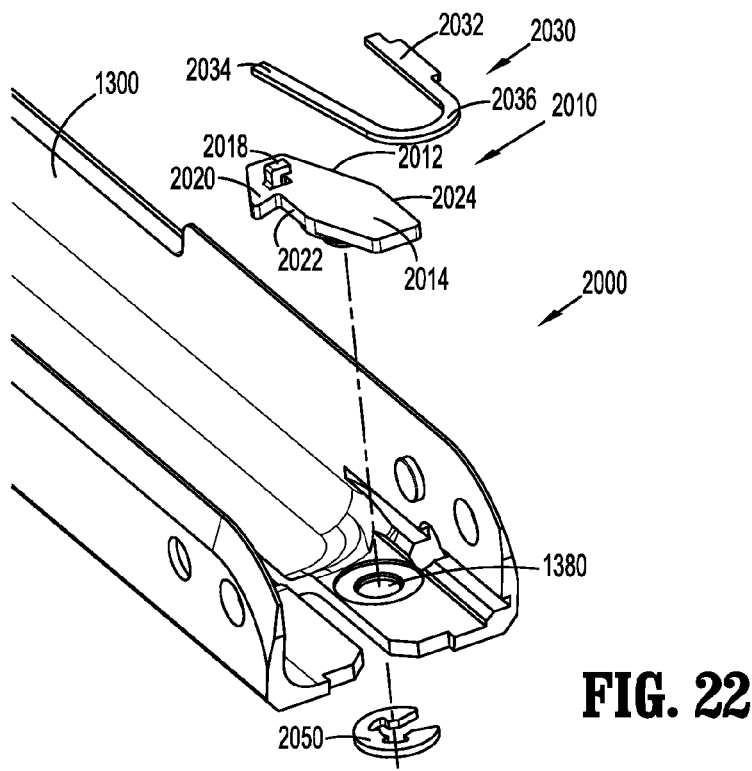
FIG. 22 is a perspective assembly view of the lockout mechanism and a portion of the channel.
Figure 23:
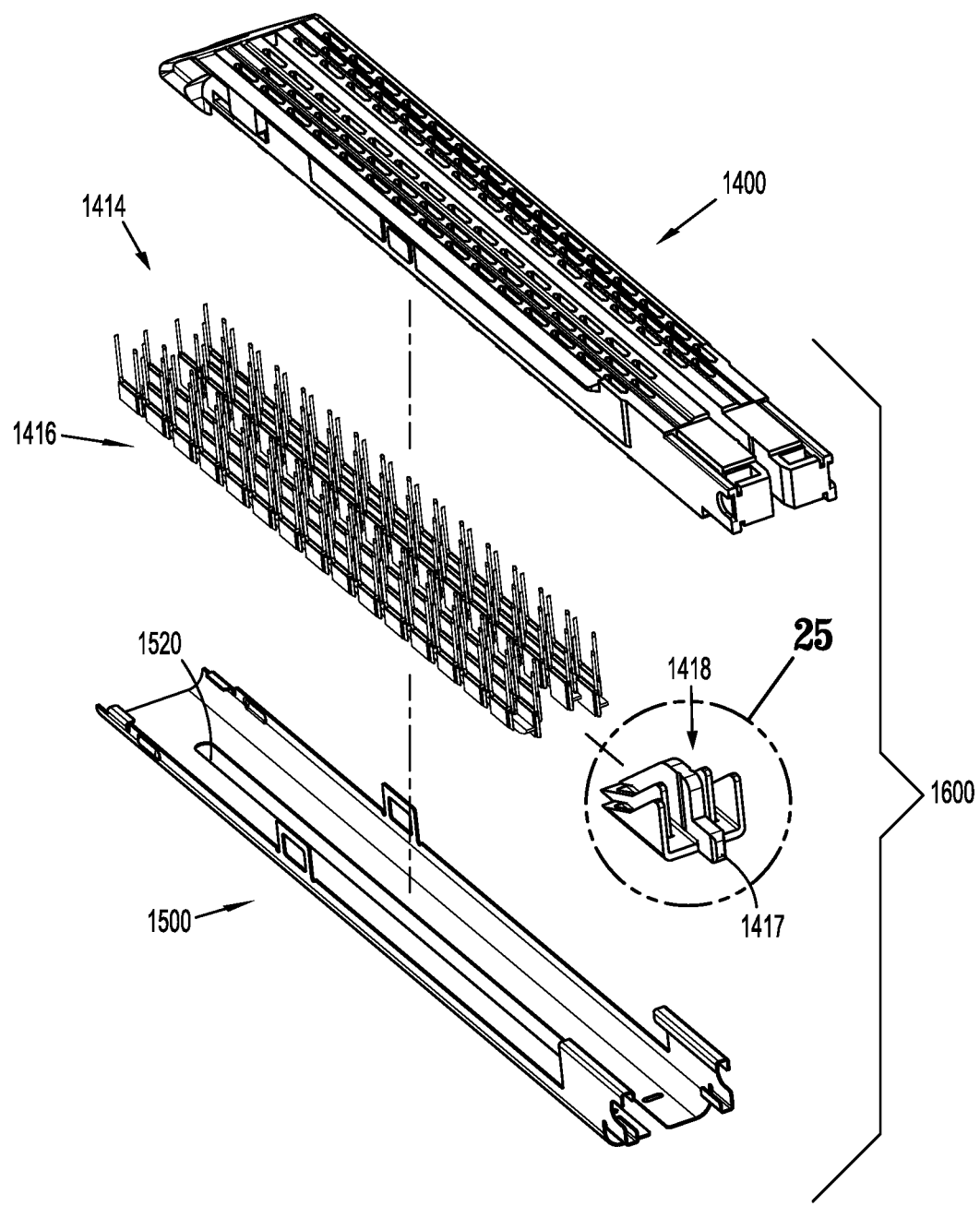
FIG. 23 is an assembly view of the removable assembly of an embodiment of the present disclosure.
Figure 24:
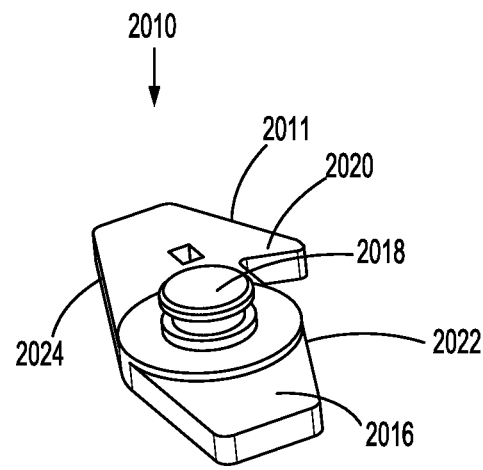
FIG. 24 is a perspective view of a latch of the lockout mechanism of the present disclosure.
Figure 25:
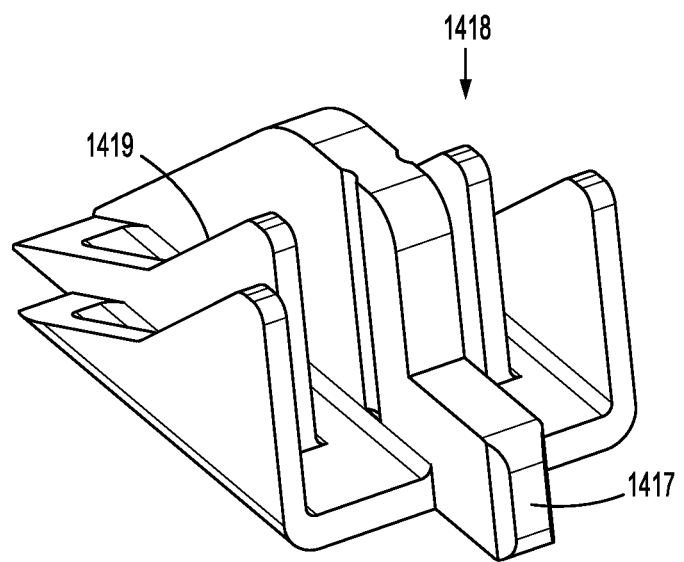
FIG. 25 is a perspective view of a sled of the present disclosure.
Figure 26:
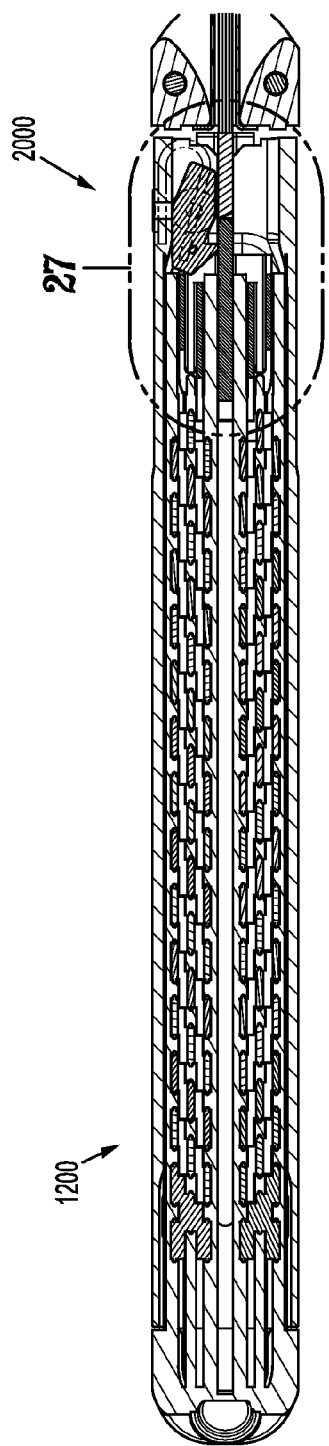
FIG. 26 is a top view of the cartridge assembly taken along line 26-26 of FIG. 18 and illustrating the lockout mechanism, and the drive member and sled in their original positions.
Figure 27:
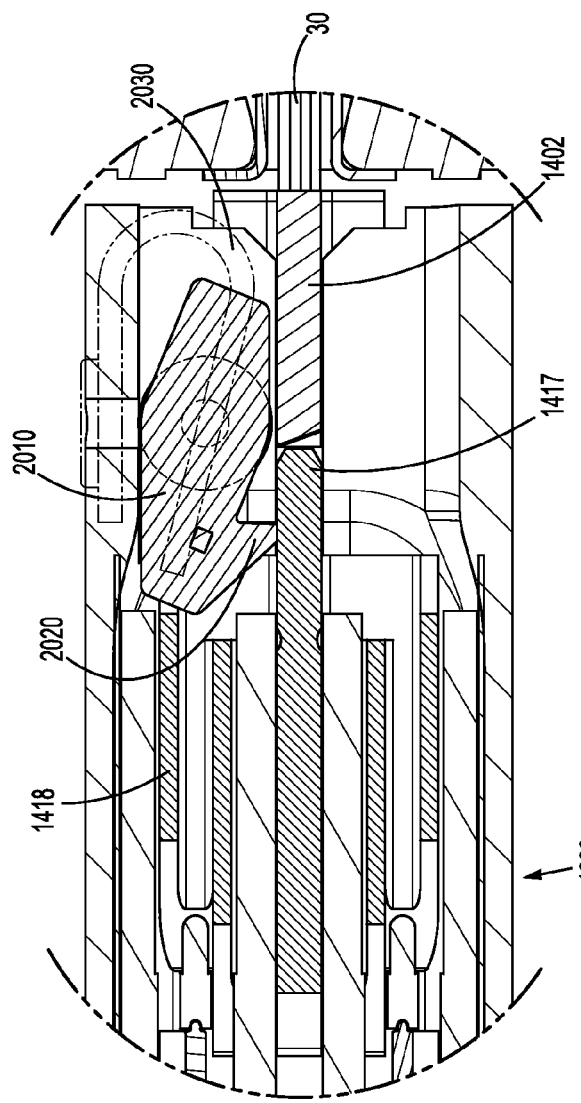
FIG. 27 is an enlarged view of the area indicated in FIG. 26.

With particular reference to FIGS. 22 and 24, latch 2010 includes a body 2012 having an upper surface 2014 and a lower surface 2016, a lower protrusion 2018 depending downwardly from lower surface 2016, a spring stop 2019 extending upwardly from upper surface 2014, and a shaped surface 2020 on a first lateral side 2022. The body 2012 also has a second lateral side 2024. The shaped surface 2020 has two sides. The first side 2020a is angled with respect to the central slot 1340 when the latch 2010 is in a blocking position in which the latch obstructs the passage of the dynamic clamping member 1402. The second side 2020b of the shaped surface 2020 extends transversely to the central slot 1340 when the latch is in the blocking position. (See FIG. 30).

Referring now to FIGS. 19-24, latch 2010 is mechanically engaged with channel 1300 so that the latch 2010 can pivot with respect to the channel 1300. In particular, lower protrusion 2018 of latch 2010 (FIG. 24) extends through an opening 1380 (FIG. 22) in channel 1300, such that latch 2010 is pivotable with respect to channel 1300. Lower protrusion 2018 is maintained in mechanical engagement with channel 1300 by a lock pin 2050 (FIG. 22). Alternatively, the protrusion can be omitted and a separate pivot pin in engagement with the body 2012 and the channel 1300 can be used.

Figure 21:
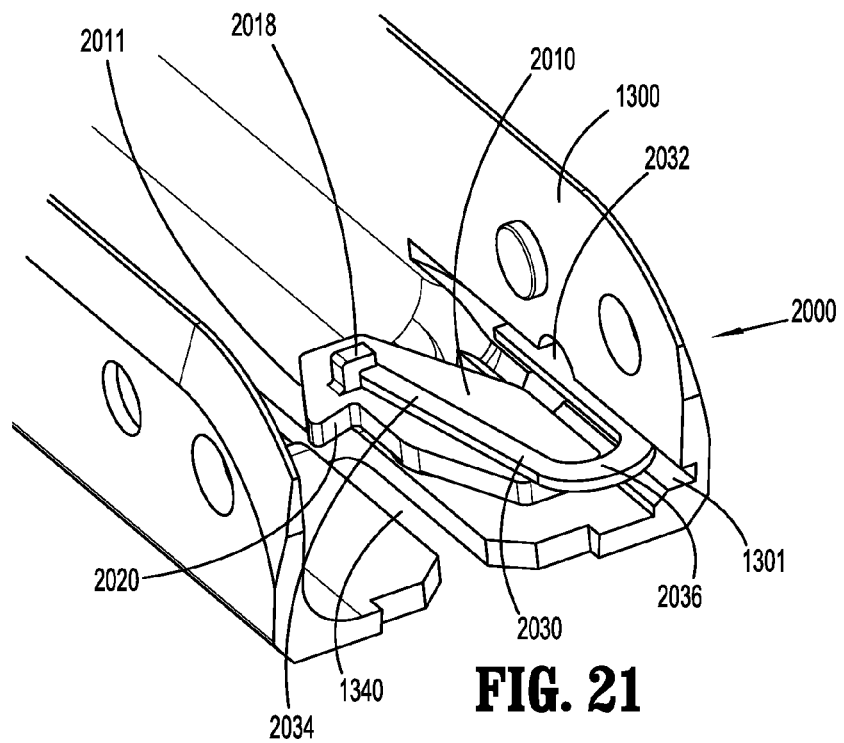
FIG. 21 is a perspective view of the lockout mechanism engaged with the channel.

With regard to FIGS. 21-22, spring 2030 includes a first leg 2032, a second leg 2034, and an intermediate portion 2036 interconnecting first leg 2032 and second leg 2034. First leg 2032 is in contact with a portion of channel 1300. For example, the channel 1300 may have a slot 1301, a notch, or some other feature for restricting the movement of the first leg 2032. Second leg 2034 is disposed in contact with spring stop 2018 of latch 2010. Intermediate portion 2036 is disposed between first leg 2032 and second leg 2034. For example, the spring may have a U-shaped configuration (see FIG. 27), or some other shape, such as L-shaped.

Spring 2030 is in mechanical cooperation with a portion of the cartridge assembly 1200. The spring is configured to bias latch 2010 towards its blocking position. In the initial position of the dynamic clamping member 1402 and the sled 1418 (e.g., prior to distal advancement thereof to fire staples and incise tissue), a tail portion 1417 of sled 1418 (FIG. 25) physically prevents the shaped surface 2020 of latch 2010 from moving from its initial position into its blocking position, and thus allows distal translation of dynamic clamping member 1402 and sled 1418 (see FIGS. 26 and 27). After translation of the dynamic clamping member and sled, the spring moves the latch 2010 to the blocking position, where the shaped surface 2020 of latch 2010 obstructs the central slot 1340 of channel 1300 and the longitudinal slot 1520 extending through base surface 1510 of support plate 1500 (see FIGS. 30 and 31), such that shaped surface 2020 would block distal translation of dynamic clamping member 1402 when the dynamic clamping member 1402 has been retracted after firing staples and cutting tissue.

The latch 2010 is laterally movable from an initial position to a blocking position. The latch moves laterally, which enables the shaped surface of the latch to obstruct the slot and move away from a position that obstructs the slot of the cartridge assembly.

During retraction of the dynamic clamping member, the dynamic clamping member slides along the shaped surface first side 2020a, keeping the latch 2010 away from the dynamic clamping member and pivoting the latch against the bias of the spring. In the retracted position of the dynamic clamping member, it is disposed proximally of shaped surface 2020 and the sled 1418 and/or tail portion 1417 is not abutting the shaped surface 2020. The latch 2010 pivots to the blocking position, so that the second side 2020b obstructs and/or prevents distal movement of the dynamic clamping member.

Figure 28:
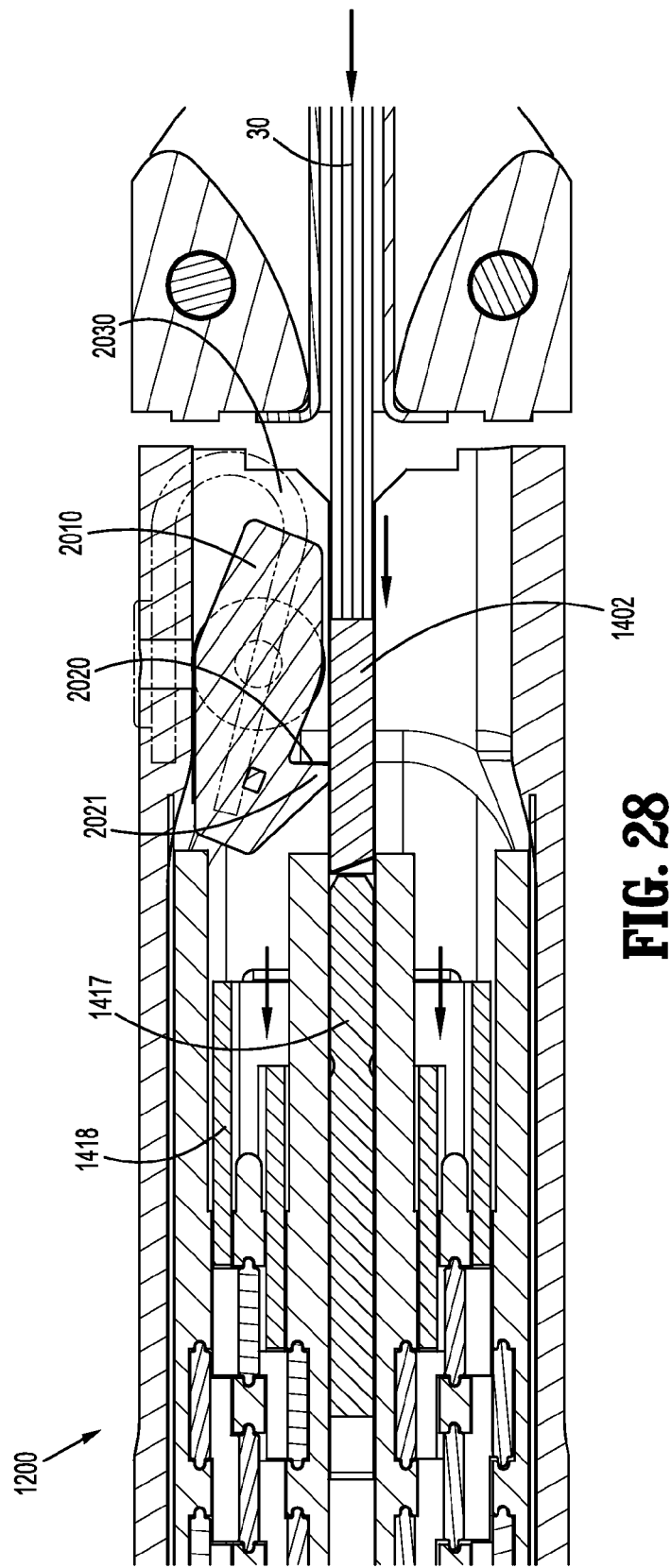
FIGS. 28-31 are top views of a portion of the cartridge assembly showing the drive member, sled, and latch in various positions.
Figure 29:
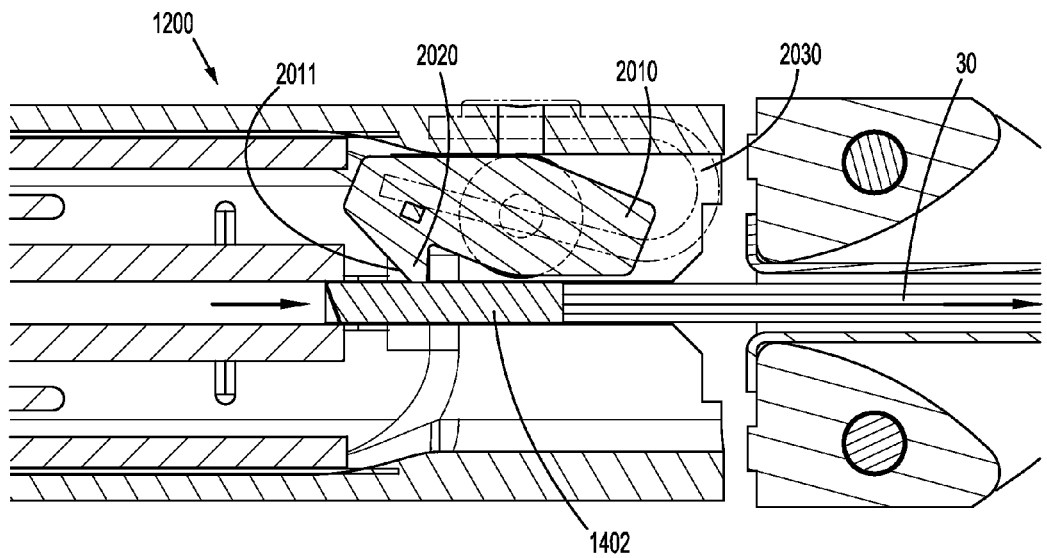
Figure 30:
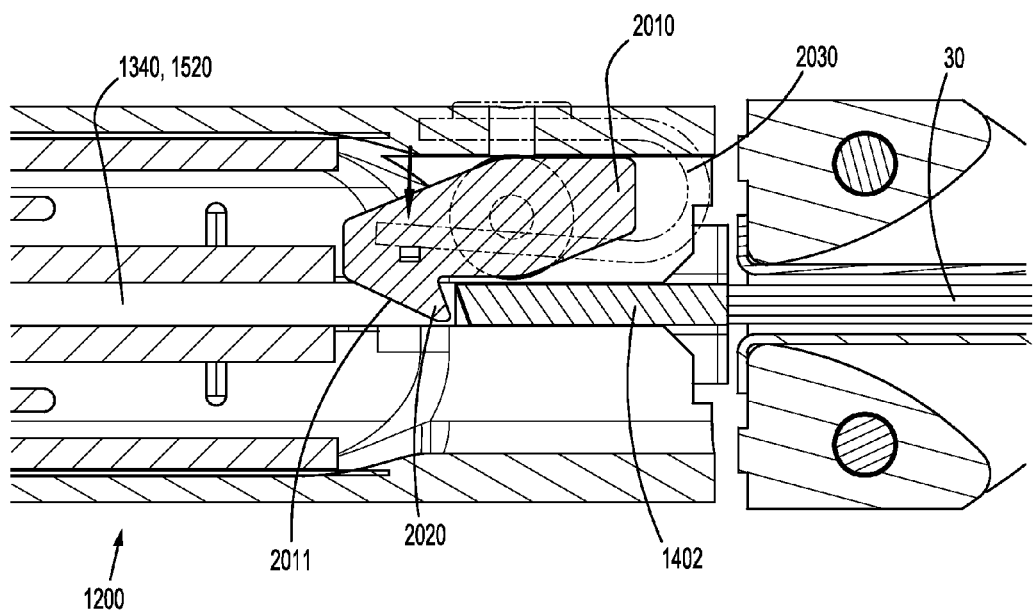

During distal advancement of dynamic clamping member 1402 and sled 1418, and after sled 1418 distally passes latch 2010 such that shaped surface 2020 is no longer in contact with tail portion of sled 1418, dynamic clamping member 1402 abuts the shaped surface 2020, which physically blocks latch 2010 from moving into its blocking position, and thus permits distal translation of dynamic clamping member 1402 (see FIG. 28).

Figure 31:
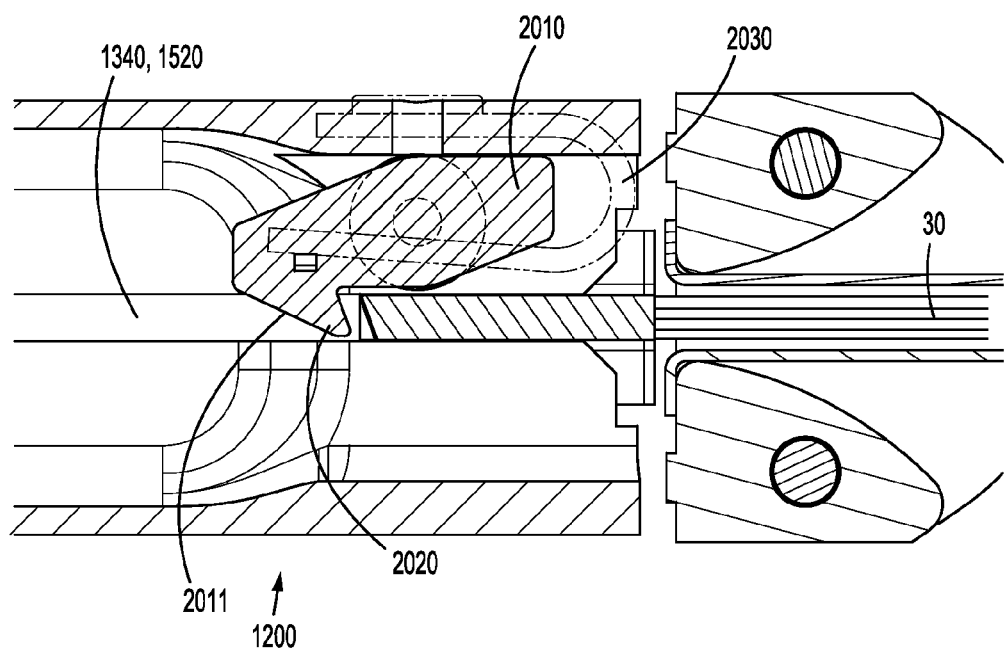
Figure 34:
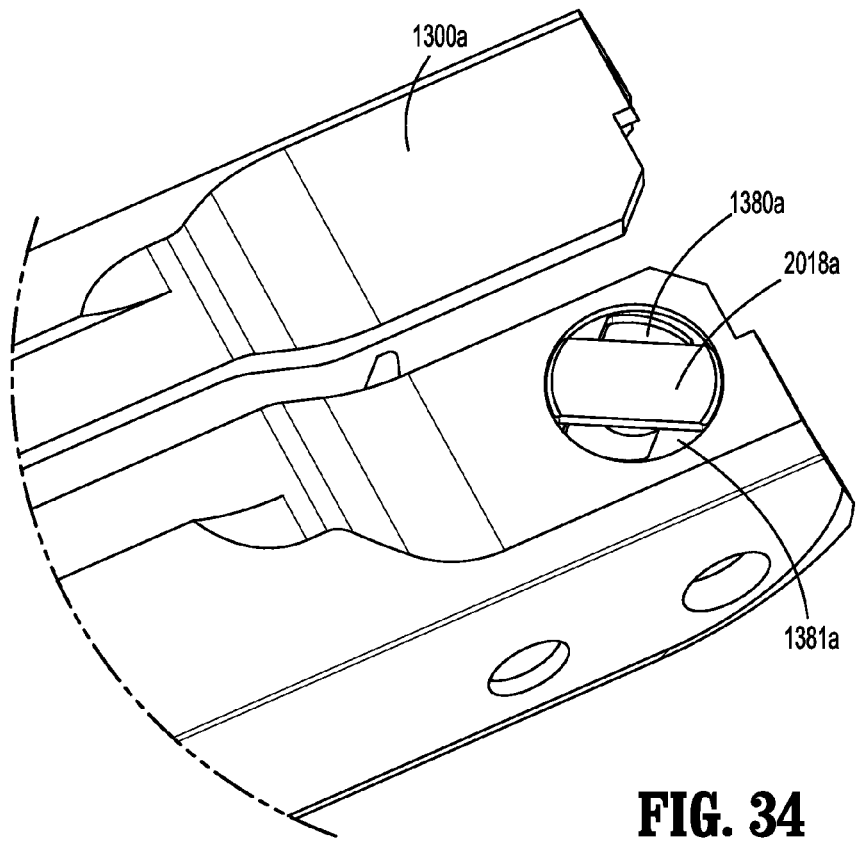
Figure 35:
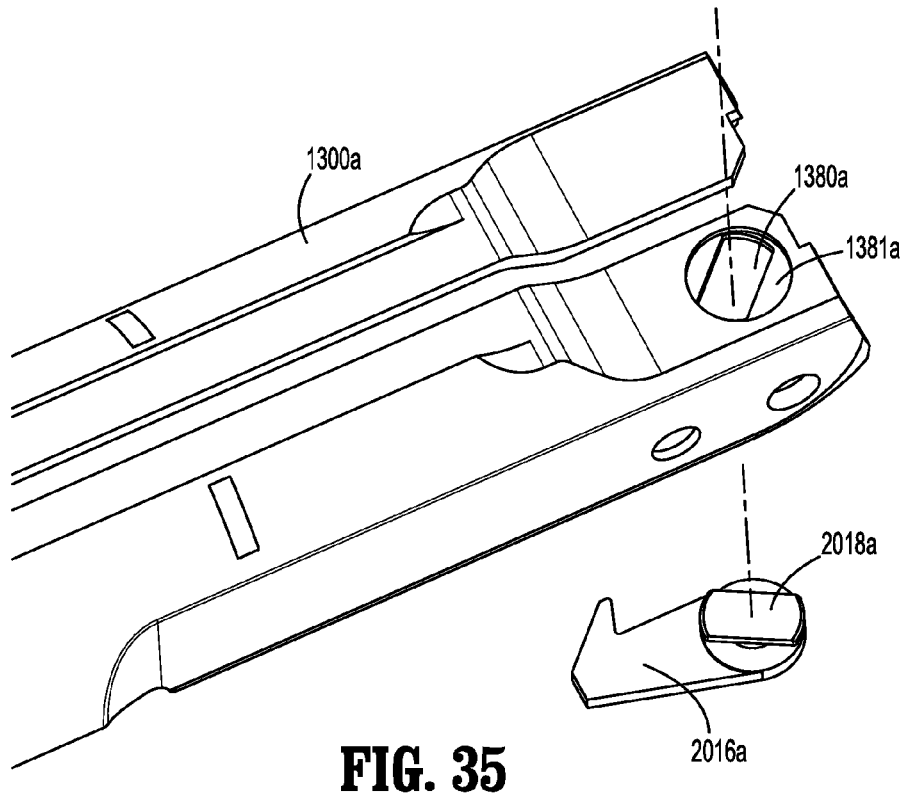

When cartridge assembly 1200 or removable assembly 1600 is removed from channel 1300, latch 2010 continues to block dynamic clamping member 1402 (see FIG. 31). When a new cartridge assembly 1200 or removable assembly 1600 is loaded onto channel 1300, tail portion 1417 of the new sled 1418 engages shaped surface first side 2020a of latch 2010 and pivots latch 2010 away from its blocking position. Without a sled having the correct configuration, the latch remains in the blocking position.

With reference to FIGS. 32-35, a second embodiment of lockout mechanism 2000a is shown. A surgical instrument having the lockout may have a channel, removable assembly, cartridge body, support plate, and the engagement structures discussed above. Furthermore, the present disclosure is directed to a removable assembly having the lockout, or a loading unit having the lockout. Lockout mechanism 2000a includes a latch 2010a, and a spring. The spring is not shown for clarity, but may be as discussed above. Unlike the embodiment of lockout mechanism 2000 discussed above, this embodiment of lockout mechanism 2000a does not include a lock pin 2050. Here, to maintain latch 2010a in engagement with channel 1300a, lower surface 2016a of latch 2010a includes a locking member 2018a depending therefrom.

In the illustrated embodiment, locking member 2018a includes a pair of parallel walls that are interconnected by a pair of arcuate walls. The opening 1380a of channel 1300a includes similar, but slightly larger shape with respect to locking member 2018a and also includes a circular recess 1381a, around which locking member 2018a can rotate (see FIGS. 34 and 35).

To engage latch 2010a with channel 1300a, locking member 2018a is inserted through opening 1380a and latch 2010a is then rotated a predetermined amount (e.g., about 40 degrees to about 130 degrees) such that latch 2010a does not fall through opening 1380a of channel 1300a. The spring (not shown in this embodiment for clarity) may then be positioned between spring stop 2018a of latch 2010a and a portion of channel 1300a, as described above.

As can be appreciated, use of surgical instrument including the second embodiment of lockout mechanism 2000a is similar to, or that same as use of the surgical instrument including the first embodiment of lockout mechanism 2000, as described above.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A surgical instrument, comprising:
   a channel including an engagement structure disposed adjacent a proximal end thereof, the engagement structure of the channel including at least one raised boss; and
   a removable assembly disposed in releasable engagement with the channel, the removable assembly comprising:
   a cartridge body configured to house a plurality of fasteners therein, the cartridge body including an engagement structure disposed adjacent a proximal end thereof; and
   a support plate configured to mechanically engage the cartridge body, the support plate including an engagement structure disposed adjacent a proximal end thereof;
   wherein the engagement structure of the cartridge body is configured for longitudinal alignment with the engagement structure of the support plate, and wherein the engagement structure of the cartridge body and the engagement structure of the support plate are configured to mechanically engage the engagement structure of the channel when the removable assembly is engaged with the channel.

2. The surgical instrument of Claim 1, wherein the engagement structure of the cartridge body includes at least one U-shaped recess.

3. The surgical instrument of claim 2, wherein the engagement structure of the support plate includes at least one U-shaped recess.

4. The surgical instrument of claim 3, wherein each of the at least one U-shaped recess of the cartridge body and the at least one U-shaped recess of the support plate includes a proximally-facing opening.

5. The surgical instrument of claim 1, wherein the channel includes a longitudinally-extending slot disposed adjacent a distal end thereof, and wherein the support plate includes an outwardly-extending finger configured to releasably engage the longitudinally-extending slot of the channel.

6. The surgical instrument of claim 1, wherein the support plate includes an inwardly-extending finger disposed on a distal portion thereof, the inwardly-extending finger configured to releasably engage a groove disposed on a distal portion of the cartridge body.

7. The surgical instrument of claim 1, wherein the support plate includes a proximal protrusion disposed adjacent a proximal end thereof, the proximal protrusion being configured to help prevent an actuation sled from prematurely translating distally with respect to the cartridge body.

8. The surgical instrument of claim 1, wherein the channel is part of a removable loading unit that includes an anvil assembly.

9. A loading unit, comprising:
   an anvil assembly;
   a channel including at least one boss disposed adjacent a proximal end thereof; and
   a cartridge assembly, at least one of the anvil assembly and the cartridge assembly being pivotable with respect to the other of the anvil assembly and the cartridge assembly, the cartridge assembly comprising:
   a support plate configured to releasably engage the channel, the support plate including at least one recess disposed adjacent a proximal end thereof; and
   a cartridge body configured to releasably engage the support plate and configured to house a plurality of fasteners therein, the cartridge body including at least one recess disposed adjacent a proximal end thereof;
   wherein the at least one recess of the cartridge body is configured for longitudinal alignment with the at least one recess of the support plate, and wherein at least one of the at least one recess of the cartridge body and the at least one recess of the support plate is configured to mechanically engage the at least one boss of the channel when the support plate is engaged with the channel.

10. The loading unit of claim 9, wherein the at least one recess of the cartridge body includes at least one U-shaped recess.

11. The loading unit of claim 10, wherein the at least one recess of the support plate includes at least one U-shaped recess.

12. The loading unit of claim 11, wherein each of the at least one U-shaped recess of the cartridge body and the at least one U-shaped recess of the support plate includes a proximally-facing opening.

13. The loading unit of claim 9, wherein the channel includes a longitudinally-extending slot disposed adjacent a distal end thereof, and wherein the support plate includes an outwardly-extending finger configured to releasably engage the longitudinally-extending slot of the channel.

14. The loading unit of claim 9, wherein the support plate includes an inwardly-extending finger disposed on a distal portion thereof, the inwardly-extending finger configured to releasably engage a groove disposed on a distal portion of the cartridge body.

15. The loading unit of claim 9, wherein the support plate includes a proximal protrusion disposed adjacent a proximal end thereof, the proximal protrusion being configured to help prevent an actuation sled from prematurely translating distally with respect to the cartridge body.

16. The loading unit of claim 9, further comprising a body portion to which the channel and the anvil assembly are attached, the body portion being attachable to an elongate member of a surgical instrument.

17. A surgical instrument, comprising:
    a channel including an engagement structure disposed adjacent a proximal end thereof and a longitudinally-extending slot disposed adjacent a distal end thereof; and
    a removable assembly disposed in releasable engagement with the channel, the removable assembly comprising:
    a cartridge body configured to house a plurality of fasteners therein, the cartridge body including an engagement structure disposed adjacent a proximal end thereof; and
    a support plate configured to mechanically engage the cartridge body, the support plate including an engagement structure disposed adjacent a proximal end thereof which is configured for longitudinal alignment with the engagement structure of the cartridge body, and the support plate including an outwardly-extending finger configured to releasably engage the longitudinally-extending slot of the channel;
    wherein the engagement structure of the cartridge body and the engagement structure of the support plate are configured to mechanically engage the engagement structure of the channel when the removable assembly is engaged with the channel.

18. A surgical instrument, comprising:
    a channel including an engagement structure disposed adjacent a proximal end thereof; and a removable assembly disposed in releasable engagement with the channel, the removable assembly comprising:
   a cartridge body configured to house a plurality of fasteners therein, the cartridge body including an engagement structure disposed adjacent a proximal end thereof; and
   a support plate configured to mechanically engage the cartridge body, the support plate including an engagement structure and a proximal protrusion disposed adjacent a proximal end thereof, the proximal protrusion being configured to help prevent an actuation sled from prematurely translating distally with respect to the cartridge body;
   wherein the engagement structure of the cartridge body is configured for longitudinal alignment with the engagement structure of the support plate, and wherein the engagement structure of the cartridge body and the engagement structure of the support plate are configured to mechanically engage the engagement structure of the channel when the removable assembly is engaged with the channel.

\* \* \* \* \*